(12) United States Patent
Kim et al.

(10) Patent No.: US 8,741,427 B2
(45) Date of Patent: *Jun. 3, 2014

(54) MICROCAVITY-CONTAINING RESILIENT, THERMOPLASTIC FOAM; COMPOSITE OF SUCH FOAM AND PARTICLES; METHODS OF PREPARING AND ARTICLES PREPARED FROM SAME

(75) Inventors: Young-Sam Kim, Midland, MI (US); Luther E. Stockton, Midland, MI (US); Mark W. VanSumeren, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 393 days.

This patent is subject to a terminal disclaimer.

(21) Appl. No.: 11/995,830

(22) PCT Filed: Jul. 13, 2006

(86) PCT No.: PCT/US2006/027373
§ 371 (c)(1),
(2), (4) Date: Jan. 16, 2008

(87) PCT Pub. No.: WO2007/011728
PCT Pub. Date: Jan. 25, 2007

(65) Prior Publication Data
US 2008/0200891 A1      Aug. 21, 2008

Related U.S. Application Data

(60) Provisional application No. 60/700,644, filed on Jul. 19, 2005.

(51) Int. Cl.
*B32B 5/18* (2006.01)
*B32B 3/10* (2006.01)
*A61F 13/15* (2006.01)

(52) U.S. Cl.
USPC .................. 428/317.9; 428/305.5; 428/315.5; 428/131; 604/358; 604/369

(58) Field of Classification Search
USPC ......... 428/305.5, 317.9, 131, 315.5; 604/369, 604/358; 3/305.5, 317.9, 131
See application file for complete search history.

(56) References Cited

U.S. PATENT DOCUMENTS 3,288,729 A   11/1966   Waterman et al.
3,669,103 A   6/1972   Harper et al.
(Continued)

FOREIGN PATENT DOCUMENTS

DE   44 18 319 A1   11/1995
EP   0 427 219 A2   5/1991
(Continued)

OTHER PUBLICATIONS

Roussy, G.G. et al., Governing Electromagnetic and Thermal Field Relations, Foundations and Industrial Applications of Microwaves and Radio Frequency Fields Physical and Chemical Processes, 1995, pp. 3-4.

(Continued)

*Primary Examiner* — Hai Vo

(57) ABSTRACT

A microcavity-containing, resilient foam comprising a thermoplastic polymer; composite structures comprising such a microcavity-containing foam and a multiplicity of particles contained in such microcavities, preferably aqueous fluid absorbent particles; methods for preparation of such foam and structures; and disposable consumer articles incorporating such foams and composites. The aqueous fluid absorbent characteristics of the foam and composite structures render them useful in the fabrication of disposable consumer articles, in particular hygiene articles designed to rapidly absorb "insults" of bodily fluid thereby conducting such fluids away from contact with the skin of the wearer of the hygiene article. The useful articles include infant and children diapers, adult incontinence pants, feminine hygiene pads, pet urine-absorbent pads and mats, household cleaning pads, surgical drapery, and the like.

17 Claims, 4 Drawing Sheets

(56) References Cited

U.S. PATENT DOCUMENTS

| | | | |
|---|---|---|---|
| 3,670,731 A | 6/1972 | Harmon | |
| 3,926,891 A | 12/1975 | Gross et al. | |
| 3,935,099 A | 1/1976 | Weaver et al. | |
| 3,997,484 A | 12/1976 | Weaver et al. | |
| 4,076,663 A | 2/1978 | Masuda et al. | |
| 4,090,013 A | 5/1978 | Ganslaw et al. | |
| 4,093,776 A | 6/1978 | Aoki et al. | |
| 4,190,562 A | 2/1980 | Westerman | |
| 4,286,082 A | 8/1981 | Tsubakimoto et al. | |
| 4,340,706 A | 7/1982 | Obayashi et al. | |
| 4,446,261 A | 5/1984 | Yamasaki et al. | |
| 4,459,396 A | 7/1984 | Yamasaki et al. | |
| 4,506,052 A | 3/1985 | Furukawa et al. | |
| 4,624,868 A * | 11/1986 | Muller | 427/384 |
| 4,654,039 A | 3/1987 | Brandt et al. | |
| 4,666,983 A | 5/1987 | Tsubakimoto et al. | |
| 4,683,274 A | 7/1987 | Nakamura et al. | |
| 4,708,997 A | 11/1987 | Stanley, Jr. et al. | |
| 4,734,478 A | 3/1988 | Tsubakimoto et al. | |
| 4,857,610 A | 8/1989 | Chmelir et al. | |
| 4,985,518 A | 1/1991 | Alexander et al. | |
| 4,990,541 A | 2/1991 | Nielsen et al. | |
| 5,145,906 A | 9/1992 | Chambers et al. | |
| 5,149,335 A | 9/1992 | Kellenberger et al. | |
| 5,629,377 A | 5/1997 | Burgert et al. | |
| 5,744,564 A | 4/1998 | Stanley, Jr. et al. | |
| 5,763,067 A | 6/1998 | Bruggemann et al. | |
| 5,788,684 A * | 8/1998 | Abuto et al. | 604/368 |
| 5,798,410 A | 8/1998 | Walther et al. | |
| 6,033,769 A | 3/2000 | Brueggemann et al. | |
| 6,288,158 B1 * | 9/2001 | Schapowalov et al. | 524/493 |
| 6,423,252 B1 * | 7/2002 | Chun et al. | 264/28 |
| 6,448,321 B1 | 9/2002 | Tokita et al. | |
| 6,765,031 B2 * | 7/2004 | Salyer et al. | 521/99 |
| 7,361,694 B2 * | 4/2008 | Strandburg et al. | 521/61 |
| 7,803,865 B2 * | 9/2010 | Moncla et al. | 524/523 |
| 2002/0002209 A1 * | 1/2002 | Mork | 521/61 |
| 2002/0058469 A1 * | 5/2002 | Pinheiro et al. | 451/526 |
| 2003/0226998 A1 * | 12/2003 | Grumbine | 252/79.1 |
| 2004/0068057 A1 | 4/2004 | Kim | |
| 2005/0192365 A1 * | 9/2005 | Strandburg et al. | 521/50 |
| 2005/0215177 A1 * | 9/2005 | Prasad | 451/5 |
| 2006/0148917 A1 * | 7/2006 | Radwanski et al. | 521/99 |
| 2007/0160833 A1 * | 7/2007 | Maak et al. | 428/343 |

FOREIGN PATENT DOCUMENTS

| | | |
|---|---|---|
| EP | 0 962 206 A2 | 12/1999 |
| GB | 1 390 180 | 11/1972 |
| WO | WO-03/022896 A1 | 3/2003 |
| WO | WO-2005/021622 A2 | 3/2005 |
| WO | WO 2005021638 A2 * | 3/2005 |

OTHER PUBLICATIONS

Saville, B.P., Shirley Stiffness Test, Physical Testing of Textiles, 1999, pp. 258-259, Woodhead Publisher, England.

* cited by examiner

MICROCAVITY-CONTAINING RESILIENT, THERMOPLASTIC FOAM; COMPOSITE OF SUCH FOAM AND PARTICLES; METHODS OF PREPARING AND ARTICLES PREPARED FROM SAME

CROSS-REFERENCE TO RELATED APPLICATIONS

This application is claiming priority from U.S. Provisional Application Ser. No. 60/700,644, filed on Jul. 19, 2005 entitled "Microcavity-Containing Resilient, Thermoplastic Foam; Composite of Such Foam and Particles; Methods of Preparing and Articles Prepared From Same," the teachings of which are incorporated by reference herein as if reproduced in full hereinbelow.

FIELD OF INVENTION

This invention relates to a microcavity-structured foam comprising a thermoplastic polymer; a composite comprising such microcavity structured foam and a multiplicity of particles; a method for preparation of such foam and articles incorporating such foams and composites.

BACKGROUND OF THE INVENTION

Superabsorbent polymers, also referred to as aqueous fluid absorbent polymers or "SAP", are primarily used in personal care products, e.g., baby diapers, adult incontinence products and feminine hygiene products. In such applications, superabsorbent polymer particles are incorporated into absorbent structures that contain synthetic and/or natural fiber or paper based woven and nonwoven structures, or toughened masses of fibers, such as fluff pads. The materials used in such structures can quickly absorb aqueous fluids and distribute them throughout the whole absorbent structure. Such structures, in the absence of superabsorbent polymers, have limited absorption capacity, are bulky due to the large amount of material needed to provide acceptable absorption capacity, and do not retain fluid well under pressure. The absorbency and fluid retention characteristics of such absorbent structures are improved by incorporating into them SAP particles that imbibe aqueous fluids to form a swollen hydrogel material.

Manufacturers of personal hygiene articles have long desired to have an absorbent core structure with a minimal thickness yet exhibiting superior absorbency capacity in the absorbent article. A thin absorbent structure is not only more economically favorable due to the reduced unit volume for transport, but also is an important factor for avoiding personal embarrassment when worn. In modern diapers, for example, manufacturers have been increasing the amount of SAP relative to the weight of the cellulose fiber component, and the quantity of the superabsorbent polymer in the diaper or other hygiene article can be 50 weight percent or higher. Various methods have been employed previously to increase the absorption capacity at reduced thickness of such an absorbent core structure. Typically, this is accomplished by using higher amounts of the SAP, but there is then a countervailing loss of wicking capability due to increased gel blocking as well as the reduced amounts of fluff capable of incorporation in such SAP-containing articles. Accordingly, previous approaches are not entirely satisfactory in achieving the desired results.

We have discovered that a microcavity-structured, open-cell foam that is suitably prepared from a frothed, aqueous dispersion of thermoplastic, preferably olefin, polymer particles, and optionally a multiplicity of fibers, exhibits a significantly improved softness, surface appearance and permeability. A microcavity structure allows particles to be placed and contained, in high concentration, in a thin foam composite. We have also found, surprisingly, that the microcavity structure of the present invention not only allows better containment of SAP particles up to high concentrations, but it also helps avoid "gel blocking". Furthermore, we also have found that treating SAP particles' surfaces with other fine particles, particularly nano-particles, surprisingly helps avoid gel blocking. One embodiment of a microcavity in a foam of the present invention is suitably of a generally cylindrical shape.

A composite of the present invention is technically relatively easy to produce. In addition to the good aqueous fluid absorption capability, its thinness and excellent softness, mechanical stability and flexibility make a composite of the invention particularly useful in diapers and various absorbent hygiene applications.

Manufacturers of personal hygiene articles also desire to have an absorbent article that can be recycled easily. Currently, commercial diapers and adult incontinence articles incorporate the absorbent core structure in such a way that the polymeric compositions and cellulose fiber must be separated first in order to be recycled after cleaning of soilage from them. The recycling process thus has been complicated, and rendered mechanically difficult, as well as uneconomical. The polymeric absorbent core structure of the present invention is considered more readily recyclable because its structure can be easily separated from soilage as well as the polymer components from one another. A diaper of the present invention is not only more economical, but also environmentally is more friendly than previous commercial diapers and other hygiene articles.

Published PCT Patent Application No. WO2005/021622 A2, 10 Mar. 2005 relates to aqueous-based froth compositions comprising dispersed olefin polymer particles, methods for preparation of such froths and the production from them of open-celled foams, laminates, and finished articles.

Foams containing SAP particles have been prepared from, for example, carboxylated styrene-butadiene latex, as described in U.S. Pat. No. 4,990,541 and European patent 0 427 219. There, superabsorbent polymer is introduced to a frothed, wet latex by spraying onto it the solid SAP powder prior to drying of the froth. That process uses a SAP powder of a particle size generally less than about 30 microns, and at a powder loading of approximately 25% based on the foam weight. Handling and processing of fine, superabsorbent powder particles of approximately 30 micrometers (microns) in size is difficult, especially on a large scale, partly because fine SAP powder rapidly absorbs moisture from the air and its particles agglomerate. Handling of such fine powder also increases potential processability issues. These include possible dust inhalation issues (respirable fines), and the issue of possible powder explosiveness that arises when a fine dust is handled. Adding and mixing SAP powder to a wet latex froth can also result in froth breakdown and any open-cell structure of resultant foam can be destroyed. Due to the quick absorption of water by the fine SAP particles, the SAP addition procedure does not permit a suitably controlled distribution of such powder on the wet foam surfaces. The relatively low amount of superabsorbent polymer that can be added to such a frothed latex also limits use of that system to those applications requiring only a relatively low absorbency capability.

U.S. Pat. Nos. 6,033,769 and 5,763,067 and German patent 4 418 319 relate to a layered foam composite comprising a water-soluble polymer foam layer and a SAP particles layer. The water-soluble polymer, typically a polyvinyl alcohol or carboxymethyl cellulose, is frothed and spread in a frothed sheet layer. Then the SAP particles are sprinkled through a template onto the froth and fixed by heat treatment. Such water-soluble polymer foams typically lack flexibility and need to be treated with a large amount of plasticizer to give a non-brittle foam; for example, a plasticizer amount of more than 200% based on the foam weight. Such water-soluble polymer foams can dissolve when contacted with aqueous liquid, causing a potential foam stability issue. Migration of such water-soluble polymer material in a hygiene article can create a slimy feeling for the user and is undesirable.

Both U.S. Pat. No. 5,149,335 and European patent 0 962 206 relate to an absorbent structure comprising containment means for aqueous fluid that can contain a relatively high concentration of SAP. The patents describe the use of a SAP with certain absorbency characteristics when it is desired to employ the SAP at relatively high concentrations. The U.S. patent employs specially agglomerated fines of SAP in an organic suspension medium. The containment means is made by pressing two layers of cellulose tissues, in which SAP particles are placed onto the bottom tissue layer in a patterned fashion and that layer is then pressed together, with the upper tissue layer bonding to the bottom layer with hot melt adhesive. The containment means described in both patents utilize a diaper design comprising an absorbent core of cellulose fluff pulp and SAP particles.

SUMMARY OF THE INVENTION

This invention relates to a composite comprising a multiplicity of particles, preferably superabsorbent polymer particles, contained in the microcavities of a microcavity-structured, preferably open-cell, foam comprising a thermoplastic polymer and optionally a multiplicity of fibers, and a method for preparation of same.

The invention also concerns a thermoplastic foam characterized by having a microcavity structure. Such a foam is suitably prepared by frothing and then drying an aqueous dispersion of thermoplastic, preferably olefin, polymer particles in a manner to introduce microcavities into the foam. Suitably, the open-cell foam is formed in a batch or continuous process, by introducing a frothed dispersion of the polymer particles into a mold that is configured with projections or indentations to cause formation, respectively, of indentations or protuberances on at least one surface of the resulting foam, which indentations/protuberances then form the basis for the resultant microcavity-structured foam. Alternatively, the microcavitied foam is prepared by a continuous process of introducing the froth onto a moving belt or onto a substrate riding on such a belt, drying the froth into a foam and subjecting the foam to an embossing roll in order to thermally emboss microcavities onto at least one surface of the foam.

The invention further comprises an open-cell foam with a microcavity structure, such foam preferably prepared using a blend of an aqueous olefin polymer particles dispersion and a multiplicity of fibers.

The invention further comprises a thin profile foam characterized by having a microcavity-structured foam with a multiplicity of particles contained in the microcavities of the foam and a method for preparation of same; a method for incorporation of particles (preferably water-absorbent particles, such as SAP) into the microcavities of a microcavity-structured foam; a method for preparation of a microcavitied absorbent core composite comprising absorbent particles contained in a microcavity-structured foam; and a method for use of the microcavitied absorbent core composite comprising absorbent particles, preferably SAP particles contained in the microcavities of a microcavity-structured foam, in various fluid-absorption applications. Such superabsorbent polymer particles absorb the fluids.

Applications for the invention are suitably in the manufacture of disposable consumer goods and articles, preferably hygiene articles, including infant and children diapers, adult incontinence products and feminine hygiene products, where the particles contained in the microcavity-structured absorbent core serve to imbibe aqueous liquids to form swollen hydrogels.

BRIEF DESCRIPTION OF THE DRAWINGS

For the purpose of illustrating the invention, there is shown in the drawings a form that is presently preferred; it being understood, however, that this invention is not limited to the precise arrangements and instrumentalities shown.

DETAILED DESCRIPTION OF THE INVENTION

Definitions

Figure 1:
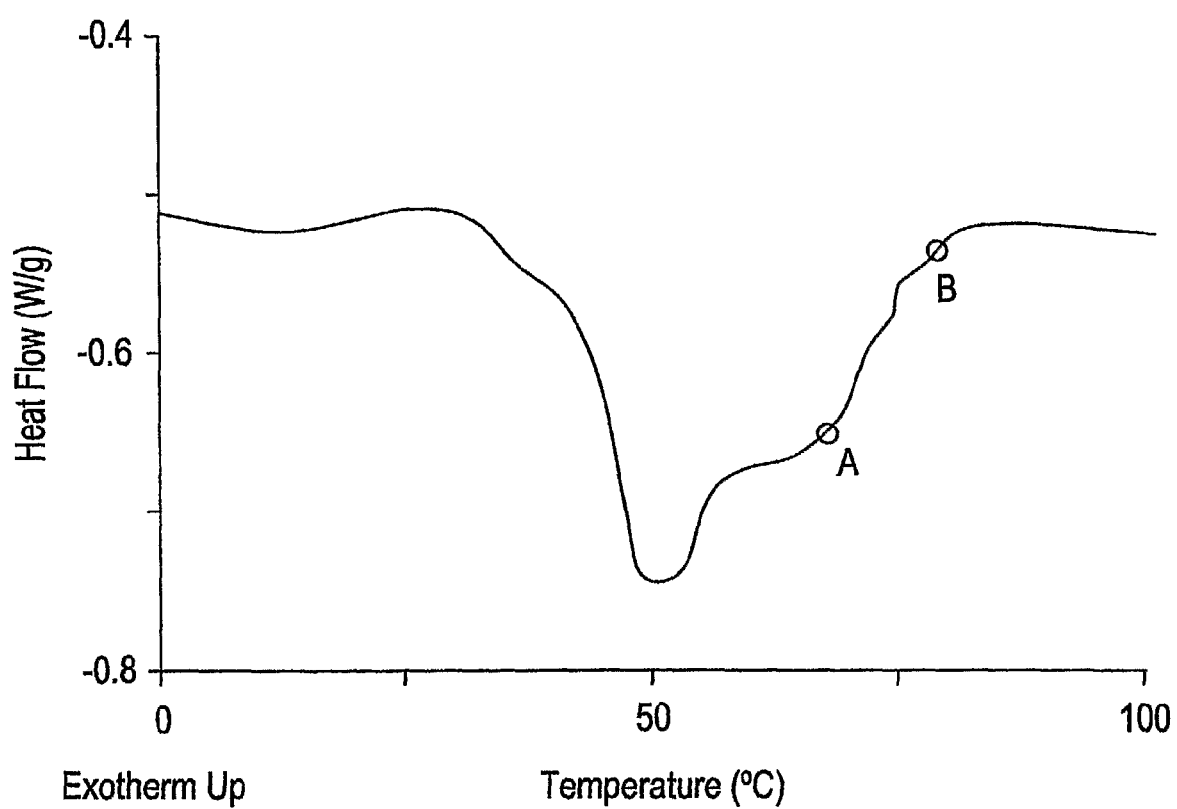
FIG. 1 exemplifies a Differential Scanning Calorimeter endotherm curve for an olefin polymer to illustrate an optimum range of the temperatures to be used in drying a frothed, aqueous particulate dispersion of that polymer.

The term "conformable" means the ability to bend and flex to the shape desired by the user; for example, the shape of a wearer of an absorbent article.

The term "dispersion" means a two phase liquid/particulate thermoplastic polymer composition where the aqueous phase is normally the continuous phase and the polymer particles are suspended therein in a stable fashion, suitably with the aid of a dispersing agent/dispersant so that the particles of polymer will remain dispersed at least for as long as it will require to complete the frothing step. Preferably, the polymer particles remain dispersed throughout the entire frothing and drying process so that a complete process can be conducted without particles of the polymer settling out of the dispersion. Suitable methods are taught in the art; see for example U.S. Pat. Nos. 5,798,410 and 6,448,321, incorporated here in by reference to the extent that they relate to such methods.

The term "drying" means a process of causing a froth to become a dry foam and the term "dry" or "dried" means elimination of at least 95 percent of the water from the froth.

The term "frothing" or "frothed" means a process of incorporating substantial volumes of air, or other gas, in an aqueous liquid where at least 80, preferably at least 85 and more preferably at least 90 volume percent of the frothed material consists of the gaseous component. The aqueous liquid can be a homogeneous solution, a micellar solution or a dispersion. In general, the froth is created by mechanical methods such as high shear mixing under atmospheric conditions or optionally injecting gas into the system while mixing.

The term "froth" means an aqueous dispersion of thermoplastic polymer particles that has been "frothed", as described above, before "drying".

The term "foam" means a structure comprised primarily of a thermoplastic polymer, and having open or closed cell cellular structure that does not collapse.

The term "Major Surface" means, in a "foam", one of two substantially parallel surfaces of largest area, in contrast to a minor surface of the foam. It is possible to cut and trim a raw foam in a manner to form a six surface, regular three dimensional cubical geometrical structure, where all six foam surfaces are of substantially the same area. However, because of the practical aspects and limitations of continuously generating a foam article, commercial foam production is suitably accomplished by spreading frothed material on a conveyer device moving in the x-direction, of y-dimension froth width, and z-dimension froth thickness. The z-axis or z-direction means the axis substantially perpendicular to the xy-plane defined by the surface of such a conveyor and therefore generally perpendicular to a Major Surface of the froth and foam as generated. Two major froth surfaces of x-length and y-width, which when dried to foam results in a three dimensional foam structure of surface area equal to about xy on both the top and bottom. It is each of these top and bottom foam surfaces that are referred to here as a Major Surface, or in the case of foam that has been slit into pieces of approximately equal thickness along the x-y axes, Major Surface means the resulting larger parallel surface on each opposite, parallel side of each of the resulting slit sheets of foam.

The term "microcavity" describes a dimensional void space on or near, (e.g., just below) a surface of the foam. The term "microcavitied" or "microcavity-containing" describes a foam or a foam structure that comprises such microcavities.

The term "open-cell foam" means a foam having an open cell content of at least 80% or greater, preferably at least 85% or greater and more preferably at least 90% or greater, as determined by and according to ASTM D2856A.

The term "polymer" means a macromolecule prepared by polymerizing monomers of the same or different type. "Polymer" includes homopolymers, copolymers, terpolymers, interpolymers, etc. The term "interpolymer" means a polymer prepared by the polymerization of at least two types of monomer. It includes, but is not limited to, copolymers (which usually refer to polymers prepared from two different monomers), terpolymers (which usually refers to polymers prepared from three different types of monomers), and tetrapolymers (which usually refers to polymers prepared from four different types of monomers), etc.

The term "monomer" or "comonomer" refers to any compound with a polymerizable moiety, which is added to a polymerization reaction in order to produce a polymer.

The term "thermoplastic polymer" or "thermoplastic composition" and similar terms such as "thermoformable polymer" mean a polymer or polymer composition that is substantially thermally extrudable or deformable.

The term "Resilient" is defined as the foam rebounding toward its original thickness i.e. it recovers at least 60%, preferably at least about 70%, more preferably at least about 80% of the original foam thickness, when the foam was compressed to half its original thickness at room temperature, e.g. about 25° C. The foam is in its dry state, i.e. a minimum moisture content of not more than about 10% weight, preferably not more than about 5% weight, moisture content, during the resiliency test.

Preparation of Superabsorbent Polymer (SAP)

The superabsorbent polymer ("SAP") particles useful in this invention are those that absorb many times their own weight of the fluid in question, such as moisture, water or aqueous liquids. SAP particles swell when they absorb the fluid. SAPs are used in a variety of applications, including diapers, water-barrier applications in the construction industry, and liquid absorbers in food-packaging systems, as well as in hygiene and medical applications. SAP particles can be any of the known hydrophilic polymers that are cross-linked and capable of absorbing large quantities of aqueous fluids, in some instances causing the particle to swell up to several times its dry size. These polymers are well known in the art and are widely available commercially. Most SAPs are crosslinked, partially neutralized and/or surface treated. Preferably, the level of crosslinking is selected to give the desired swelling characteristics for the particular application.

Examples of some suitable SAPs and processes (including gel polymerization processes) for preparing SAPs are disclosed in U.S. Pat. Nos. 3,669,103; 3,670,731; 3,926,891; 3,935,099; 3,997,484; 4,076,663; 4,090,013; 4,093,776; 4,190,562; 4,286,082; 4,340,706; 4,446,261; 4,459,396; 4,654,039; 4,683,274; 4,708,997; 4,857,610; 4,985,518; and 5,145,906, the teachings of which are incorporated herein by reference. In addition, see Buchholz, F. L. and Graham, A. T., "Modern Superabsorbent Polymer Technology," John Wiley & Sons (1998) and Lisa Brannon-Peppas and Ronald S. Harland, "Absorbent Polymer Technology" Elsevier (1990).

The SAP may be in the form of particles or other forms, such as fibers. Preferably, the SAP is in the form of particles and is derived from one or more ethylenically unsaturated carboxyl-containing monomers and optionally one or more comonomers copolymerizable with the carboxyl-containing monomer.

SAPs advantageously are derived from one or more ethylenically unsaturated carboxylic acids, ethylenically unsaturated carboxylic acid anhydrides or salts thereof. Preferred unsaturated carboxylic acid and carboxylic acid anhydride monomers include acrylic acid, methacrylic acid, itaconic acid, maleic acid, fumaric acid and maleic acid anhydride. More preferably the starting monomer is acrylic acid, methacrylic acid or a salt thereof. Additionally, SAPs may include comonomers known in the art for use in superabsorbent polymers or graft copolymers including comonomers such as an acrylamide, an acrylonitrile, a vinyl pyrrolidone, a vinyl sulphonic acid, an acryloxyethyltrimethyl ammonium chloride or a salt thereof, and graft substrates such as a cellulose, a modified cellulose, a polyvinyl alcohol or a starch hydrolyzate. If used, the comonomer may comprise up to 25 percent by weight of the monomer mixture.

Preferably, about 50 mole percent or greater of the carboxylic acid units of the superabsorbent polymer are neutralized with base, and more preferably about 65 percent or greater. This neutralization may be performed after completion of polymerization. In a preferred embodiment, the starting monomer mix has carboxylic acid moieties that are neutralized to the desired level prior to polymerization. The final polymer or the starting monomers may be neutralized by contacting them with an alkali metal hydroxide, for example, sodium hydroxide or potassium hydroxide, or an alkali metal carbonate, for example, sodium carbonate or potassium carbonate.

The superabsorbent polymers are lightly crosslinked to make them water-insoluble. Vinyl, non-vinyl or dimodal crosslinkers can be employed, either alone, as mixtures, or in various combinations. The total amount of all crosslinkers present is sufficient to provide a polymer with good absorptive capacity, good absorption under load, and a low percent of extractable materials.

Polyvinyl crosslinkers known in the art for use in SAPs and the preferred vinyl crosslinkers for SAPs include, but are not limited to, e.g., bis(meth)acrylamides, allyl(meth)acrylates, di- or poly-esters of (meth)acrylic acid with polyols, such as diethylene glycol diacrylate, trimethylol propane triacrylate and polyethylene glycol diacrylate; and di- or polyesters of unsaturated mono- or poly-carboxylic acids with polyols derived from the reaction of $C_1$-$C_{10}$ polyhydric alcohols with 2 to 8 mols of $C_2$-$C_4$ alkylene oxide per hydroxyl group, such as ethoxylated trimethylol propane triacrylate.

The non-vinyl crosslinkers that can be employed in making superabsorbent polymers are agents having at least two functional groups capable of reacting with the carboxyl groups of the polymer, and include materials such as glycerin, polyglycols, ethylene glycol diglycidyl ether, and diamines. Many examples of these agents are given in U.S. Pat. Nos. 4,666,983 and 4,734,478 which teach the application of such agents to the surface of absorbent polymer powder followed by heating to crosslink surface chains ("surface-crosslinking") and improve absorption capacity and their dispersion/absorption rate. Additional examples are given in U.S. Pat. No. 5,145,906, which teaches surface-crosslinking with such agents. The non-vinyl crosslinkers can be added homogeneously to the polymerization mixture at the start of the process. Preferred non-vinyl crosslinkers include, but are not limited to, glycerin, ethylene glycol diglycidyl ether, polyethylene glycol 400 and polyethylene glycol 600. Mixtures of non-vinyl crosslinkers can be employed.

The dimodal crosslinkers that can be employed in the preparation of SAPs are agents that have at least one polymerizable vinyl group and at least one functional group capable of reacting with carboxyl groups. They are called "dimodal crosslinkers" to distinguish them from normal vinyl crosslinkers, because they use two different modes of reaction to form a crosslink. Examples of dimodal crosslinkers include, but are not limited to, hydroxyethyl methacrylate, polyethylene glycol monomethacrylate, glycidyl methacrylate and allyl glycidyl ether. The dimodal crosslinker advantageously is added homogeneously to the reaction mixture at the start of the polymerization process. Mixtures of dimodal crosslinkers can be employed.

Another component of the aqueous medium used to prepare the superabsorbent polymers comprises a free radical initiator, which may be any conventional water-soluble polymerization initiator. For example, peroxygen compounds such as sodium, potassium and ammonium peroxodisulfates, caprylyl peroxide, benzoyl peroxide, hydrogen peroxide, cumene hydroperoxide, tertiary butyl diperphthalate, tertiary butyl perbenzoate, sodium peracetate and sodium percarbonate. Conventional redox initiator systems can also be utilized, e.g., formed by combining the foregoing peroxygen compounds with reducing agents, such as sodium bisulfite, sodium thiosulphate, L- or iso-ascorbic acid or a salt thereof or ferrous salts. Preferably the initiator comprises from 0.001 to 0.5 mole percent, based on the total moles of polymerizable monomer in the aqueous medium. Mixtures of initiators can be employed.

In one preferred mode of SAP preparation, at least one chlorine- or bromine-containing oxidizing agent is added to the monomer mixture or to the wet hydrogel to reduce the amount of residual monomers in the final SAP. It is preferably added to the monomer mixture. A preferred oxidizing agent is a chlorate salt with potassium and/or sodium counter ions. Chlorine-containing oxidizing agents are preferred. Preferably, 100 ppm by weight or greater and more preferably 200 ppm or greater, of a chlorine-containing oxidizing agent is used, based on the total weight of monomers. Desirably, the amount of a chlorine-containing oxidizing agent added is most preferably 500 ppm or less. The oxidizing agent is present in sufficient amount such that after heat-treatment, the residual monomer level is reduced and the desired balance of centrifuge retention capacity and AUL properties is achieved.

SAPs can be prepared in a batch or continuous manner. The batch polymerization can be performed in a manner where all of the reaction materials are contacted simultaneously and the reaction proceeds, or it may take place with the continuous addition of one or more of the components during the reaction period. WO 03/022896 publication contains a description of a continuous process for SAP preparation. Preferably, the polymerization is performed under an inert gas atmosphere, for example, nitrogen or argon. The reaction may be performed at any temperature that the polymerization occurs, preferably 25° C. or greater and more preferably 50° C. or greater. The reaction is conducted for a time sufficient to result in the desired conversion of monomer to the crosslinked SAP. Preferably, the conversion is 98 percent or greater. Advantageously, initiation of the reaction occurs at a temperature of at least 0° C.

It is possible to carry out the polymerization process using multiphase polymerization processing techniques such as inverse emulsion polymerization or inverse suspension polymerization procedures. Inverse suspension polymerization procedures are described in greater detail in U.S. Pat. Nos. 4,340,706; 4,506,052 and 5,744,564. When inverse suspension polymerization or inverse emulsion polymerization techniques are employed, additional ingredients such as surfactants, emulsifiers and polymerization stabilizers suitably are added to the overall polymerization mixture.

During polymerization, the SAP generally absorbs all of the aqueous reaction medium to form an aqueous hydrogel and is removed from the reactor in that form. The term "hydrogel" refers to a water swollen superabsorbent polymer, and can be in the form of polymer particles. Preferably, the hydrogel comprises 25 to 45 percent by weight polymer, with the remainder being water (as determined by weight loss after drying the hydrogel at above 100 deg C. for at least an hour or by weight gain upon hydration of dry polymer particles). The hydrogel is preferably processed into a particulate shape during the polymerization reaction process in the reactor by the agitator or other means in order to facilitate the removal of the hydrogel from the reactor. Particle sizes of the hydrogel range preferably from 0.01 to 10 cm. More preferably, particle sizes of the hydrogel range from 0.05 to 0.3 cm. In multiphase polymerization, the SAP hydrogel particles may be recovered from the reaction medium by azeotropic distillation and/or filtration followed by drying. If recovered by filtration, means commonly known in the art of removing solvents present in the hydrogel are then used.

After removal from the reactor, the hydrogel polymer is subjected to comminution, for example, by a convenient mechanical means of particle size reduction, such as grinding, chopping, cutting, or extrusion. The size of the gel particles after particle size reduction should allow homogeneous drying of the particles. Preferably, the particle size reduction is performed by extruding the hydrogel.

The comminuted hydrogel polymer particles are subjected to drying conditions to remove the remaining polymerization medium and any dispersing liquid including the optional solvent and substantially all of the water. Desirably, the moisture content of the SAP after drying is between zero and 5 weight percent.

The drying temperature is a temperature high enough to remove the liquid polymerization media, including water and optional solvent, in a reasonable time period, yet not so high so as to cause degradation of the SAP particles, such as by breaking of the crosslink bonds in the polymer. Preferably, the drying temperature is 180° C. or less and desirably is 150° C.

or above. The drying time should be sufficient to remove substantially all of the liquid media. Preferably, the drying time ranges from 20 minutes to 60 minutes. Drying is performed under conditions such that water, and optional solvent, volatilizing away from the absorbent polymer particles are removed. This can be achieved by the use of vacuum techniques or by passing inert gases or air over or through the layers of polymer particles. In a preferred embodiment, the drying occurs in dryers where heated air is blown through or over layers of the polymer particles. Preferred dryers are fluidized beds or belt dryers or a drum dryer may be used. Alternatively, the water may be removed by azeotropic distillation. Such techniques are well known in the art.

During drying, the SAP particles may form agglomerates and may then be subjected to comminution, for example, by mechanical means for breaking up the agglomerates. Such means can include chopping, cutting and/or grinding. In a preferred embodiment, the dried polymer particles are chopped and then ground. The dried and ground particle size preferably ranges from 0.1 mm to 0.8 mm. Dried particles can be used as the basis polymer for further core/shell treatment. Modern second generation SAPs are manufactured by giving polymer particles a core/shell structure. The formation of the shell can be made by various techniques, one being the application of a surface crosslinking to the dried and ground SAP particles, which originally have a crosslinking density that may be assumed to be essentially uniform throughout the particle. A microscopic technique for visualizing such core/shell structure of surface crosslinked water-absorbent polymers is presented by Y.-S. Kim in the proceedings of INDEX 99 Congress (April 1999), Geneva Switzerland.

This surface crosslinking technology is of commercial importance and is based on the formation of new covalent bonds in surface regions, e.g., by esterification of the pendant carboxylic groups with various reagents at elevated temperatures. Surface crosslinking is any process that increases the crosslink density of the polymer in the vicinity of the water-absorbent polymer particle surface with respect to the crosslinking density of the particle interior. The surface crosslinked water-absorbent polymer particles typically are prepared by varying surface crosslinker type and concentration. Preferred surface crosslinkers include chemicals with one or more reactive functional groups that are reactive towards pendant groups (typically carboxylic acid groups) of the polymer backbone chains. An example is the use of polyhydric compounds, e.g., glycerin, added in an aqueous isopropanol mixture to the surface of dried and sized particles. Treated particles are then heated to around 200 deg C. for several minutes. Esterification of pendant groups can also be accomplished by the use of diglycidyl or organic carbonate compounds, e.g., ethylene glycol diglycidyl ether, or ethylene carbonate, respectively, in aqueous solution for surface crosslinking.

A typical approach is to add a coating mixture of surface crosslinking agent and a solvent and/or water to the surface of dry particles. The amount of surface crosslinker suitably is from about 0.01 to about 4 wt %, and preferably from about 0.1 to about 2.0 wt % based on the weight of the dry water-absorbent polymer. The organic solvent and/or aqueous organic solvent mixture improves the uniformity of the crosslinker distribution. Typical organic solvents are lower alcohols, and include methanol, ethanol, 2-propanol and butanol, as well as mixtures of these alcohols. Because formation of a uniform surface shell on each individual particle is highly desirable, the crosslinking reaction most suitably occurs after the desired particle size distribution has been achieved. The depth of penetration, and therefore the resulting shell thickness, can be controlled to some extent by the water content in the coating mixture. In the alcoholic solution in which the surface crosslinker agent or a mixture of surface crosslinker agents is dissolved, alcohol typically is used in an amount of 0.1 to 6.0 wt % and/or water an amount of 0.1 to 6 wt %, both based on the weight of the dry water-absorbent polymer. The amount of alcohol employed is preferably kept as low as possible to protect against a danger of explosion. The main consequences of surface crosslinking are believed to be formation of a shell of higher crosslinking density with a certain shell thickness. Coated particles are then heated in a mixer, such as paddle mixer, fluidized bed mixer, twin-screw mixer at a temperature between about 120 and 220° C. for from a few minutes to 60 minutes or longer, depending on the temperature applied. As a result, a more rigid surface layer is formed which can prevent or inhibit gel particles from gel-blocking during swelling. Consequently, the particles' absorbency under load (AUL) improves.

In the surface crosslinking reaction step, additives of inorganic and organic nature can be added to the mixture in order to modify the surfaces of the polymer particles. Examples of additives are inorganic and/or organic additives including, for example, silicates, calcium carbonate, zinc oxide, calcium phosphate, aluminum oxide, magnesium oxide, titanium dioxide, clays, cyclodextrin, activated carbon, zeolites, bentonite, kaolin, chlorophyllin and various water-soluble polymers, biocides and odor control agents.

Another type of surface crosslinking technology that has been used in the SAP manufacture is ionic surface crosslinking. Ionic surface crosslinking uses the fact that polyvalent cations can associate with more than one carboxylic group on polycarboxylated chains. The polyvalent metal salt is preferably water-soluble, and preferred metal cations include the cations of Ca, Mg, Al, Zn, Zr and Ti. Preferably, the metal cation has a valence of at least +3. A trivalent cation, such as aluminum, is most preferred. Preferred anions in the polyvalent metal salt include halides, acetate, and sulfate. Aluminum sulfate is the most preferred polyvalent metal salt. The aluminum sulfate salt is commercially available as a hydrated aluminum sulfate, having 12 to 14 waters of hydration. Preferably aluminum sulfate is used as an aqueous solution, which has a concentration of from about 5 to 49 weight percent.

Ionic surface crosslinking reactions are generally room temperature processes. In this technology, the dried and optionally heat-treated SAP particles are surface treated with aluminum sulfate or other polyvalent metal salts. Water-absorbent polymer and polyvalent metal salt are mixed, using routine blending techniques. The water-absorbent polymers can typically comprise 0.1 to about 8 wt % of a polyvalent metal salt based on the weight of the dry water-absorbent polymer. In the dry blending step a binder, which may for example be mineral oil, propylene glycol, glycerin, or poly (ethylene glycol), can be added to the mixture. In the dry blending step, the mixture of polyvalent metal salt and water-absorbent polymer can also be combined with fine particulate additives of various types of inorganic and organic nature and in various particle morphologies, as noted above elsewhere, in order to modify the surfaces of the polymer particles.

To increase the flowability of dried SAP particles silicon dioxide, preferably fumed silica, or other fine inorganic or organic powders may be mixed with the polymer particles. Any other powdery additives are desirably added to and mixed with the polymer particles together with the fumed silica. The fumed silica is preferably used in amounts of from 0.01 to 5, and more preferably from 0.05 to 3 weight percent, all based on dry polymer. An exemplary fumed silica is Aerosil R972, available from Degussa AG, Germany. The additives may be added dry or in the form of an aqueous dispersion.

In another embodiment, a core/shell structured particle is achieved by a thermally controlled degradation of the polymer network in the presence of special oxidizing agents as taught in U.S. Pat. No. 5,629,377. With this technology, the core/shell structure is thought to be formed by decreasing the core crosslinking density while the surface crosslinking density remains unchanged or is even increased. For instance, sodium or potassium chlorate used as the oxidizer is added prior to polymerization so that they are present uniformly in the resulting dried particles. The oxidizer ('chlorate') is substantially inert through the polymerization and drying process step, but is then activated during a subsequent heat treatment step. In this technology, dried and ground SAP particles containing chlorate are subjected to a heat-treatment step after drying and optional particle size reduction. Heat-treatment provides a beneficial increase in the AUL of the SAP, particularly the AUL under higher pressures. Controlled chain scission of the polymer network, in the core region by activated chlorate, is thought to lead to a core/shell structure in the particle. The absorbency properties of the SAPs made by the chlorate technology are comparable to properties achieved with surface crosslinking technology. Suitable devices for heat-treatment include, but are not limited to, rotating disc dryers, fluid bed dryers, infrared dryers, agitated trough dryers, paddle dryers, vortex dryers and disc dryers. The time period and temperature of the heat-treatment step are chosen such that the absorption properties of the polymer are improved as desired. The polymers are desirably heat-treated at a temperature at about 220° C. or above but 235° C. or below. The polymers are heated to the desired heat-treatment temperature and preferably maintained at such temperature for 10 minutes or more, but for not more than about 40 minutes.

If available SAP particles do not have suitable properties, e.g., the desired particle size, centrifuge retention capacity and/or absorbency under load (AUL) (both as measured in 0.9 wt. % NaCl solution at room temperature), then particles having such properties normally can be prepared from available SAP particles by suitable treatment means, e.g., milling, screening, and/or subjecting the SAP to one or more of heat-treating, surface crosslinking, and/or ionic crosslinking processes, as described above.

Preparation of Microcavity-Containing Foam

The invention foam comprises microcavities on or near at least one surface of the foam and these microcavities are suitably created by the simple forming technique taught in greater detail, below. Near the surface, as used herein, refers to a distance of at least 1 micron from any surface of the foam. A major portion of the microcavities is preferably of a generally uniform size. Also, preferably the microcavities are arranged in a substantially uniform pattern on or near at least one surface of the foam.

Referring to FIGS. 2 a-d, a simple means of forming microcavities in foams of the invention is to spread the foam's precursor froth into a mold of desired shape that has multiple promontories, protuberances or projections and/or depressions or indentations extending, respectively, from and/or into at least one face of that mold. Such face then forms the mold surface adjacent to the froth and ultimately the foam surface upon which the microcavity structure will become permanently imprinted, as a reverse image, upon drying. Accordingly, the shape of the microcavities that result on the foam surface after drying of the precursor froth, can easily be predetermined in design of the mold. Referring to FIG. 3, there is shown a drawing (not to scale) representing the microcavitied foam that can be prepared from such a frothing/drying/molding process, using such a mold. Obviously, a mold projection will create a corresponding depression and a mold indentation will create a corresponding protuberance on the adjacent foam surface.

Figure 2D:
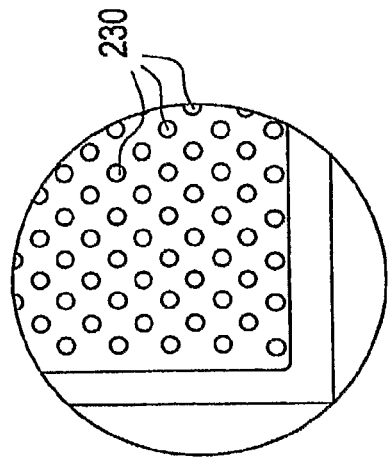
FIGS. 2 a-d show a mold useful for the preparation of microcavity-structured foam from a frothed, thermoplastic polymer aqueous dispersion.
Figure 2A:
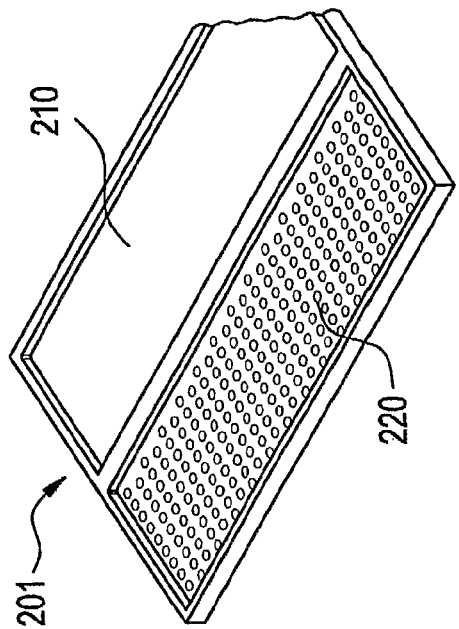
Figure 2B:
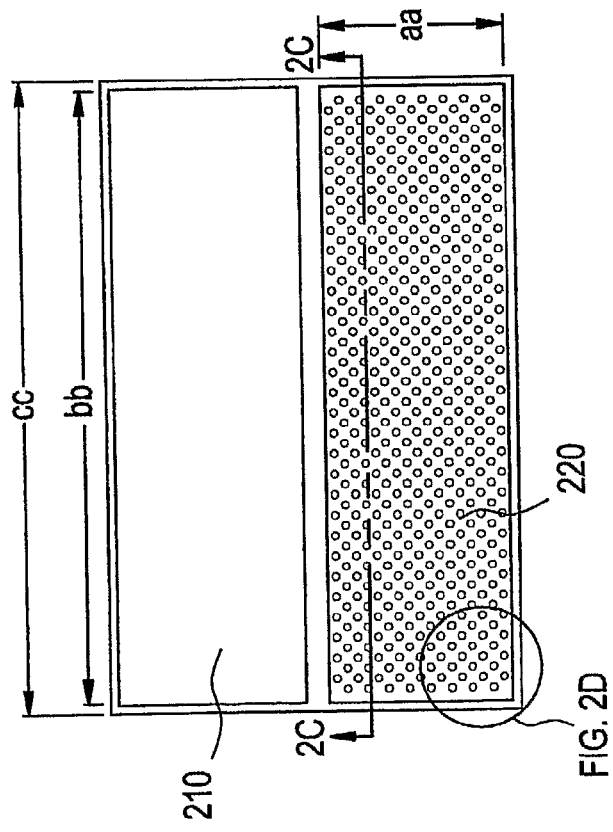
Figure 2C:
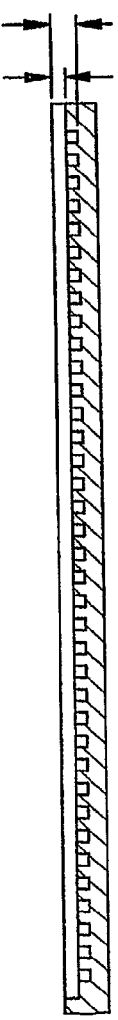
Figure 3A:
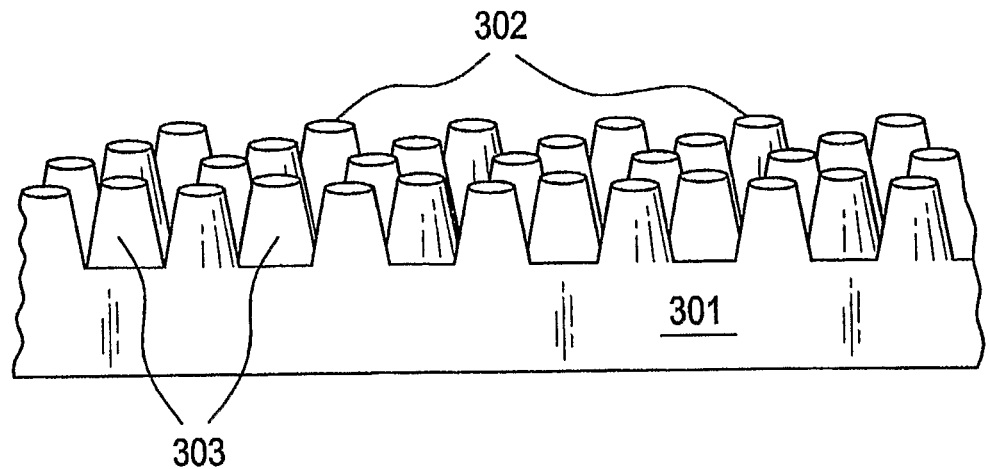
FIGS. 3 a-b show a microcavity-structured foam, with particles contained in the microcavities.
Figure 3B:
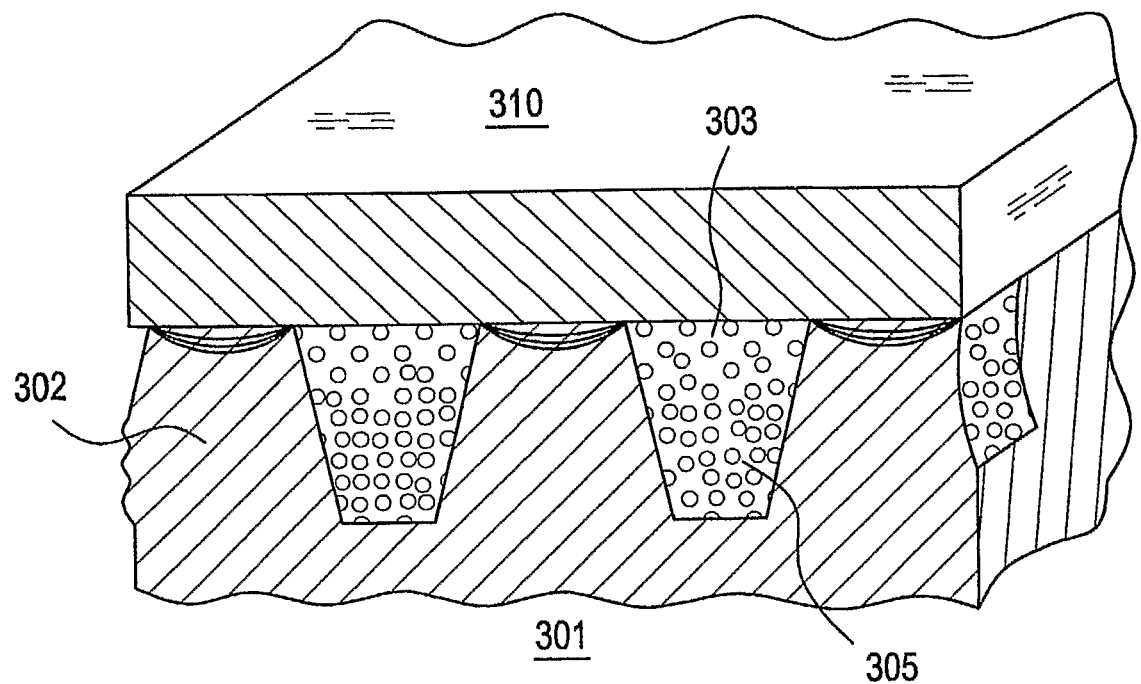

Referring to FIGS. 3 a-b, consequently, the approximate shape and size of the resulting microcavities 303 in the resulting resilient foam can also be predetermined in design of the shape and the size of those features of the mold. A microcavity of generally cylindrical shape is easily obtained by use of a suitably designed mold, such as shown in FIGS. 2 a-d. FIGS. 3a and 3b have microprojections 302 and resultant microcavities 303 represented as cone shapes, rather than as cylinders from the mold found in FIGS. 2 a-d, because it is more apparent in such representations how particles are constrained in the microcavities.

The average diameter or opening size of the foam's microcavities, as measured by a mechanical gauge, optical microscopy, scanning electron microscopy (SEM) or as predetermined in design of the mold, is suitably at least 0.1 mm or greater; preferably at least 1 mm or greater; more preferably at least 2 mm or greater; and is suitably less than or equal to 10 mm; preferably less than or equal to 5 mm; and more preferably less than or equal to 3 mm.

The average depth of the foam's microcavities, as measured by a mechanical gauge, optical microscopy or scanning electron microscopy (SEM) method, or as predetermined by the mold design, is suitably at least 0.5 mm or greater; preferably at least 2 mm or greater; more preferably at least 3 mm or greater; and is suitably less than or equal to 10 mm; preferably less than or equal to 7 mm; and more preferably less than or equal to 5 mm.

The total void volume in the foam, cumulatively occupied by the microcavities in that foam is suitably at least 5%, preferably 7% or greater, more preferably 9% or greater, most preferably 12% or greater; and suitably is 29% or less, preferably 25% or less, more preferably 22% or less, even more preferably 18% or less, and most preferably 14 percent or less, of the foam's total volume.

Referring to FIGS. 3 a-b, the total void volume for microcavities 303 in the foam can be calculated as follows.

$$\text{Percent total void volume} = V_{MC}/V_{Tot} \quad \text{[Equation (1)], where:}$$

$V_{Tot}$=total volume of microcavitied frothed foam in cm$^3$= (l)×(w)×(D); l=length of the foam in cm w=width of the foam in cm D=depth of the foam in cm; and $V_{MC}$=total volume of microcavities in cm$^3$=(N)×[(π)× (r$^2$)]×(d)

N=numbers of microcavities r=radius of the microcavity in cm d=depth of the microcavity in cm.

The invention further comprises a resilient foam structure where particles, preferably particles of an absorptive material ("absorbent particles"), more preferably fluid absorbent particles, are trapped or essentially confined in the voids formed by the microcavities on or near at least one surface of the foam. The term "confined", "constrained" or "contained" as used here is intended to convey the concept that such particles are not able to freely move from the surface of the foam, yet are not necessarily embedded within or firmly attached to the individual cells of the foam and normally are capable of restricted movement within the confines of each microcavity—being suitably constrained or restricted in their lateral movement by the walls of each such microcavity.

As noted, microcavities are situated on or near, as defined hereinabove, at least one surface of the foam. They may be situated on or near, as defined hereinabove, more than one such surface. For simplicity of manufacture and assembly, formation of the microcavities on or near, as defined hereinabove, only one surface, preferably a major surface, is desirable. Referring to FIG. 3b, there are shown microcavities 303 formed between the projections 302 of a microcavitied foam structure 301, which can be loaded with particulate material.

In a particular embodiment, where microcavities are formed at/on, as defined hereinabove, a surface of the precursor froth and the resulting resilient foam after drying, the microcavities will have at least one cavity "wall" open toward the mold surface and in effect "facing away" from the foam surface. In such an embodiment, referring to FIG. 3b, the open "wall" is suitably closed by the application of a cover member 310, preferably a layer comprised of the same or another flexible absorptive foam material, which layer 310 is attached in suitable fashion to cover and enclose the microcavitied foam surface. Particles 305 situated within the microcavities 303 are thereby constrained in the substantially closed microcavities space formed between the projections 302, the foam surface and the covering layer 310 as if "caged." Some communication of a limited quantity of particles, between individual adjacent microcavities, is not detrimental to the general useful absorptive nature of the resulting foam structure. However, a gross migration of the particles, from a large number of microcavities in one area to another area of void space defined by the microcavities, could result in a poor distribution of the absorptive capability of such particles and an uneven fluid flux across that foam surface. Consequently, a gross communication of particles from multiple microcavities to others is not desired. Generally, particle movement is to be discouraged for uses of the particle-containing foam in hygiene and medical applications, e.g., as absorbent media/elements in diapers, surgical drapery, and the like.

The cover member 310 may be prepared from any material, construction, and configuration suited to the intended use for the structure, as long as the particles are thereby appropriately constrained. Examples of the cover member construction 310 include, but are not limited to, webs, sheets, and films, preferably of permeable and/or absorbent material including foam, a woven or a non-woven layer and composites of same.

The instant invention more preferably includes a resilient foam, comprised of at least one ethylene interpolymer, the foam containing a multiplicity of microcavities on or near at least one of its surfaces, which microcavities cumulatively comprise the percentages of the foam's total volume as noted in greater detail, above. An aqueous-based, dispersed thermoplastic polymer froth precursor for the foam is suitably prepared from particles of a semi-crystalline, thermoformable polymer which imparts a recyclable character to the resulting resilient foam.

The microcavitied, open-cell foam composition of the invention is a resilient foam. It may be obtained from drying of an aqueous, frothed dispersion of particles of the thermoplastic polymer under conditions selected to inhibit coalescence of the individual gas bubbles in the froth for a time period sufficient to allow dispersed thermoplastic polymer particles contained in the thin aqueous layer surrounding the entrapped air bubble to fuse in a mold of suitable configuration before the aqueous film structure undergoes significant collapse. The frothing process may take place under any conditions, for example, the frothing process may take place below the melting point of the thermoplastic polymer or at room temperature, e.g. 25° C.±10° C. The froth may have any viscosity; for example, the froth may have a viscosity of less than 50,000 centipoises. All individual values and subranges less than 50,000 centipoises are included herein and disclosed herein; for example, the froth may have a viscosity of less than 30,000 centipoises; or in the alternative, the froth may have a viscosity of less than 20,000 centipoises. Drying occurs as the water evaporates from the bubbles' surfaces and from the channels or interstices between the bubbles.

Preferred modes of use and articles comprised of the microcavitied, thermoplastic foam include aqueous-fluid absorbent, conformable hygiene articles, more particularly baby diapers, adult incontinence products, feminine hygiene products, nursing pads, household cleaning pads, pet urine-absorbent mats used to, for example, line a pet litter box, etc. or individual urine-absorption pads for pets, sweat bands, wiping toweling and sponges, wound dressing pads, surgical sponges, medical garments and surgical drapery as well as for absorbent padding for food packaging and waste disposal. Such padding typically is employed for absorbing meat juice and drippings at the bottom of food packaging trays and, for example in disposable refuse/garbage bags. The foam is also useful in time-release delivery systems, for example as in sustained delivery of pharmaceutical and drug products, as through skin contact patches and the like.

The invention further comprises recyclable, absorbent articles. In the case of generally non-disposable articles of a more permanent and reusable character, such as sound and thermal insulation and cushioning applications, in particular, the recyclable nature makes the absorbent foam a very attractive material from which to fabricate articles. This is due to their other fluid absorption-related properties, for example, in automobile seat cushioning, headliners and sound insulation components, carpet backing for autos or homes, furniture cushioning and mattresses and padding, gas or liquid filtering devices and similar applications.

Thermoplastic Polymers

Thermoplastic polymers used in preparation of foam of the invention can be any of those that can be molded or formed into a resilient foam having microcavities on or near, as defined hereinabove, a surface of said foam. Quite suitably adapted for use in the invention is a semi-crystalline olefin polymer, selected from interpolymers of ethylene and/or propylene and other monomers selected from $C_4$ to $C_{20}$ olefins, preferably alpha-olefins such as isobutene, 1-butene, 1-hexene, 4-methyl-1-pentene, 1-heptene, 1-octene, 1-nonene and 1-decene, even more preferably alpha-olefins of from $C_4$ to $C_8$, and most preferably from the alpha-olefins n-butene, n-hexene and n-octene. The ethylene or propylene content of the polymer ranges from about 2-98 weight percent of polymer. Where a softer, more flexible foam is desired a primarily ethylene-based polyolefin is selected in which ethylene comprises from about 98 to 65 percent of polymer. Where a stiffer foam of greater flexural modulus is desired, a primarily propylene-based polyolefin may be selected, propylene comprising from about 98 to 65 percent of the polymer. Selected comonomer(s) make up the remainder of the polymer. One particularly preferred thermoplastic polymer is a copolymer of ethylene with a comonomer selected from $C_3$ to $C_8$ alpha-olefins.

The preferred group of olefin polymers to be utilized in the invention has the following characteristics and properties:
1) Crystallinity as determined by the observance of at least one endotherm when subjected to standard differential scanning calorimetry (DSC) evaluation (see, for illustration purposes, FIG. 1);
2) for ethylene-based polymers a melt index ("MI") determined according to ASTM D1238 at 190 deg C. (375 deg F.) with a 2.16 kg (4.75 lb) weight (i.e., condition 190 C./2.16 kg) of about 30 or less, preferably of about 25 or less, more preferably of about 22 or less, and most preferably of about 18 g/10 min or less and about 0.1 or greater, preferably about 0.25 or greater, more preferably about 0.5 or greater, and most preferably about 1 g/10 min or greater; and for propylene-based polymers a Melt Flow Rate ("MFR") determined according to ASTM D1238 at 230 deg C. (446 deg F.) with a 2.16 kg (4.75 lb) weight (i.e., condition 230 C./2.16 kg) of about 85 or less, preferably of about 70 or less, more preferably of about 60 or less, and most preferably of about 50 g/10 min or less and about 0.25 or greater, preferably about 0.7 or greater, more preferably about 1.4 or greater, and most preferably about 2 g/10 min or greater; and 3) for ethylene-based polymers a density, according to ASTM D 792, of about 0.845 or greater, preferably about 0.85 or greater, more preferably about 0.855 and most preferably about 0.86 g/cc or greater, and about 0.925 or less and preferably about 0.91 g/cc or less, more preferably about 0.905 or less, and most preferably about 0.90 g/cc or less; and for propylene-based polymers because density is a less commonly used measure of the backbone composition than for ethylene polymers, a propylene-based polymer comprises about 5 percent or greater, preferably about 7 percent or greater and about 35 percent or less, preferably about 25 percent or less comonomer content.

One class of olefin polymers particularly suited to use in the invention are copolymers of ethylene and 1-octene, 1-hexene, 4-methyl-1-pentene or 1-butene, where ethylene comprises from about 90 or less, preferably about 85 or less to about 50 or greater, preferably about 55 or greater, and such comonomer comprises from about 10 or greater, preferably about 15 or greater to about 50 or less, preferably to about 45 or less, percent by weight of the copolymer, and those copolymers that have Melt Index of about 0.25 or greater, preferably about 0.5 or greater and about 30 or less, preferably about 20 or less g/10 min.

Another particularly preferred class of polymers for use in the invention are copolymers of propylene and ethylene, 1-octene, 1-hexene, 4-methyl-1-pentene or 1-butene, where propylene comprises from about 95 or less, preferably about 93 or less to about 65 or greater, preferably about 75 or greater, and the comonomer comprises from about 5 or greater, more preferably about 7 or greater to about 35 or less, preferably 25 or less percent by weight of the copolymer, and those copolymers that have a Melt Flow Rate of about 0.7 or greater, preferably about 1.4 g/10 min or greater and about 85 or less, and preferably about 55 g/10 min or less.

Alternatively, instead of a single polymer a blend of polymers may be employed that has the physical characteristics described above. For example, it may be desirable to blend a first polymer with relatively high MI or MFR that is outside the range described above, with another of relatively low MI or MFR, so that the combined MI or MFR and the averaged density of the blend fall within the ranges noted above. A more crystalline alpha-olefin polymer may be combined with one of relatively lower crystallinity, such as one having a significant amount of long chain branching, to provide a blend that has substantially equivalent processing capability in preparing stable froth and resilient foam of the invention.

Where reference is made to a "polymer" in this specification, it is understood that blends of polymers with equivalent physical characteristics may be employed with like effect and are considered to fall within the scope of our invention. In a more preferred embodiment, at least one ethylene-based polymer is blended with one or more second ethylene-based polymers.

A particularly preferred class of polymer, when used without other polymers or film forming additives, is characterized by exhibiting a particular type of DSC plot of the polymer's endotherm. In the preferred class, referring to FIG. 1, the observed endotherm exhibits a relatively gentle slope as the scanning temperature is increased past the final endotherm maximum (i.e., the last inflection point on the DSC curve, e.g., point A found on FIG. 1, where the curve slope becomes positive and the curve then returns to baseline state). This reflects a polymer of broad melting range rather than a polymer having what is generally considered to be a sharp melting point.

The average particle size of the thermoplastic polymers particles used in preparation of an aqueous dispersions of same suitably is equal to or greater than about 0.1 micron, preferably equal to or greater than 1 micron, more preferably equal to or greater than 1.5 micron; and suitably equal to or less than 10 microns, preferably equal to or less than 5 microns, and more preferably equal to or less than 2 microns.

Examples of suitable ethylene polymers for use include, but are not limited to, Ziegler-Natta type polymers such as DOWLEX, ASTUTE, and FLEXOMER. Examples of so-called metallocene polymers include EXACT, AFFINITY and ENGAGE and even EXCEED. Other types of polymers suitable for use include vanadium catalyzed polymers such as TAFMER. Propylene based polymers which can be used include VISTAMAXX and VERSIFY. New Olefin Block Copolymers made by The Dow Chemical Company, trademarked INFUSE, are also useful to make the foams of the invention. Blends of these polymers can also be used such as blending with other types of block copolymer such as SEBS, SBS, SIS, etc., including partially or fully hydrogenated block copolymers. One such polymer is trademarked KRATON. Other polymers suitable for use, either alone or in blends include ethylene/carboxylic acid (e.g., acrylic or methacrylic acid) copolymers and ionomers made therefrom, and even traditional high pressure low density polyethylene (LDPE).

Other Components and Additives

For given type of SAP fines, surface modifying the SAP particles with other fine particulates, for example fumed silica particles that are micron sized particles comprising agglomerated silica nano-particles, results in better wicking for a composite structure upon contacting with aqueous liquid, when compared with the same SAP fines used without surface treatment. For surface treatment of SAP fines, fumed silica and Magadiite and modified Magadiite particles are especially useful. The improved wicking length upon contacting with aqueous liquid from the superabsorbent composite structure is especially useful in applications for which the absorbency of the superabsorbent polymer fines is utilized.

Fine particulates can assume the morphology of platelets, tubes of different characteristic length, e.g., nano-carbon tubes, cylinders, polycylinders, spheres, balls e.g., fullerene types, polyhedrals, discs, needles, polyneedles, cubes, irregular shapes or ellipsoids of various inorganic and/or organic materials.

Surfaces of the SAP can be modified by various types of additives. Also, inorganic and/or organic powder additives, for example silicates, calcium carbonate, titanium dioxide, clays, cyclodextrin, activated carbon, zeolites, chlorophyllin and various water-soluble polymers, biocides, and odor control agents may be added either directly to the raw materials to prepare the froth or may be added to and contained in the microcavities of the resulting foam. Such inorganic and/or organic additives may, if so desired, be added separately to the foam microcavities without the inclusion of SAP particles. Fibers made from cellulosic base stock, e.g., cotton linters/staple fibers, and/or polypropylene may be suitably incorporated into froth used to prepare the foam in order to provide added strength and flexural modulus to the foam or to reduce or eliminate cracking in the drying foam.

Testing Procedures/Methods

Unless otherwise indicated, the following test procedures are suitably employed to measure the characteristics and performance of superabsorbent polymer particles and of foam samples as well as the performance of foam composite samples that comprise superabsorbent polymer particles constrained in microcavities of the foam structure. Except where otherwise stated, percentages and parts are based on weight.

Superabsorbent Polymer ('SAP') Material

A superabsorbent polymer that may suitably be employed in the invention is DRYTECH ST10 brand superabsorbent polymer. It is commercially available from The Dow Chemical Company and has a particle size approximately between 100 and 850 micrometers i.e., ~100-850 microns, (hereafter called 'Polymer A').

In some embodiments, the superabsorbent polymer used is prepared by sieving through a 500 micron and onto a 100 micron sieve so that the final SAP comprises a size fraction falling approximately between 100 and 500 microns (hereafter called 'Polymer B').

A finer sized SAP material (hereafter called 'fines') used in certain embodiments is obtained from a commercial plant during the manufacturing of a superabsorbent polymer normally as a by-product, when a dried and ground SAP product is screened prior to heat treatment. The particle size distribution of the fines is rather broad and the particle size is smaller than approximately 315 microns (hereafter called 'Polymer C'). Such fines are shown in published U.S. patent application 2004/068,057 A1.

In some cases, the Polymers A, B or C are subjected to a surface treatment procedure with inorganic and/or organic powder additives, for example silicates, calcium carbonate, titanium dioxide, clays, cyclodextrin, activated carbon, zeolites, chlorophyllin and/or various water-soluble biocidal odor control active agents or water-insoluble polymeric odor control active agents, as described below.

Superabsorbent Polymer Particles Surface Treatment

Dry (200 grams) Polymer C particles are placed at room temperature into a 500 mL glass bottle. Fumed silica (2.0 g of AEROSIL R972, available from Degussa-Huels Company, Germany) is added with agitation to the polymer powder, primarily to enhance particle flowability. When other of the above-noted inorganic and/or organic powdered additives and odor control agents are used, they are added to this mixture of the respective Polymers A, B or C, etc. and the fumed silica. The mixture of Polymers and fumed silica, with or without other additives, is then blended for 30 minutes on a sample roller (U.S. Stoneware Inc., USA).

In another embodiment, dry Polymer is surface treated using aluminum ions. Polymer powder (2.0 kg) is placed at room temperature into a Forberg blender that has a mixing volume of approximately 2500 mL, a shaft with rotor blades and a nozzle. A 48.5 wt percent aluminum treatment solution is prepared, by dissolving 485 g $Al_2(SO_4)_3 \cdot 14H_2O$ in 515 g of distilled water. To each Polymer sample, 125 g of the aluminum sulfate solution (6.25% active aluminum, based on dry Polymer) is sprayed directly onto the Polymer particles and the mixture is blended for 15 min. When other powder or particulate additives, e.g., cyclodextrin, activated carbon, chlorophyllin, etc. are used, they are added to a mixture of the Polymer and aluminum sulfate solution. The blender contents are then blended for 15 minutes.

Centrifuge Retention Capacity (CRC)

Superabsorbent polymer particles (300 mg) are sieved to a size range of 30-50 U.S. standard mesh, giving a range of SAP particles of approx. 300 to 600 micrometers (microns) average particle size, and are placed within a heat sealable "tea bag" (63.5 mm by 76.2 mm) (Grade 7291, available from Ahlstrom Fibercomposites, Chimside, Dunes Berwickshire, Scotland). If SAP fines are tested, the sample is used as is. The tea bag is heat-sealed using a heated element on all four edges and the SAP particles are distributed evenly throughout the bag by holding it horizontally and tapping it gently. A saline solution (2 liters) of sodium chloride solution (0.9%) is poured into a stainless steel utility tray with approximate dimensions of 42 cm×25 cm×6.4 cm. The tea bag is immersed for 30 minutes in the saline solution. The tea bag is removed from the saline solution and then centrifuged for three minutes at 1600 rpm. The weight of saline solution absorbed is determined by difference in the weight of the tea bag with the dry particles, and the weight of the bag and particles after centrifugation. The weight ratio of saline solution absorbed to weight of dry SAP particles is the centrifuge retention capacity (CRC) and is recorded in gram solution per gram of dry SAP particles (g/g).

Absorbency Under Load (AUL)

A 50 mm by 50 mm nylon screen (100 mesh/ca. 150 microns) is put on top of a perforated metal plate (with 5 mm diam. holes) followed by a filter paper (30 mm diam., Whatman No. 1) and finally by a stainless steel cylinder (open at both ends) of 25.4 mm inner diameter, 37 mm outer diameter and a height of 50 mm. SAP particles (167 mg) of a 30-50 mesh size fraction (range of about 300 to 600 microns) are placed into the cylinder and evenly distributed, then covered by a nonwoven plastic fiber mat of a fiber diameter of 26 mm and pressed down with a plastic piston of 26 mm diameter of known weight. The total weight of piston is 109.4 grams to give a 2.1 kPa (0.3 psi) load on the particles. The metal plate with the product in the cylinder on top is immersed in an aqueous 0.9 weight percent saline solution, in a manner such that the nylon screen and the water surface are at the same level. In this fashion, the filter paper and the superabsorbent polymer particles are able to absorb water without the influence of any hydrostatic pressure. A soak time of one hour is applied. The plate is removed from the water reservoir and the excess water in the holes of the plate and in the nylon screen is removed by soaking it up with separate paper tissues. Then the weight is removed from atop the swollen gel and the gel is weighed. The weight ratio of saline solution absorbed under load to the weight of dry SAP particles determined is reported (in g/g) as the absorption under load (AUL) for each different weight loading.

Swollen SAP Gel Layer Permeability

This test is used to measure the relative susceptibility of SAP particles, after treatment, to gel swelling. This provides a comparable means for determining the relative differences in gel blockage of microcavity-containing foam structures that incorporate such treated SAP particles in their microcavities. The permeability test cylinder consists of the following: A transparent acrylic cylinder of 2.54 cm (1 in) internal diameter and 15.24 cm (6 in) height and open at both ends, with a 100 mesh screen affixed to one end and a metric ruler affixed along the height is prepared. A 30-50 mesh (about 600 to 300 microns) cut of SAP particles is employed. SAP samples of 0.160 gram±0.0005 gram are measured and placed into the pre-tared, permeability test cylinder. The vertical cylinder is gently tapped until the SAP granules are evenly distributed within the cylinder bore.

A 150 g aliquot of 0.9% saline solution is added to a 250 mL beaker. About 2.5 cm of the screened end of the permeability cylinder is gently and gradually submerged in the beaker of liquid until the polymer has wet out. Then, the cylinder is further submerged until it is almost touching the bottom of the beaker, and at that level the cylinder is clamped to a vertical ring stand. The cylinder and contents is allowed to soak for 30 minutes.

After soaking, the cylinder is removed from the liquid and a nylon mesh with an approximate diameter of 2.4 cm is placed inside the cylinder on top of the swollen gel polymer. Then a plastic, perforated acrylic piston (4.153 grams, 2.136 cm diameter containing 19 holes of a diameter of 1.588 mm each) is placed into the permeability cell atop the nylon mesh. A weight of a generally triangular cross-section and sized to apply 2.1 kPa (0.3 psi) pressure across the base of the acrylic piston (e.g., a 100 gram scalloped brass weight, with multiple channels along the longitudinal axis of its outer surface and a cylindrical plug reamed out through and along the longitudinal axis of the brass weight to allow the free flow of liquid through and around the remainder of the metal body thus formed) is added to the cell by lowering the weight gently until it sits atop the upper surface of the piston. The cell is then allowed to sit for about 30 seconds, after which time the height of the swollen gel is recorded in centimeters (L). The cylinder is carefully filled to its open end with the 0.9% sodium chloride solution previously noted, so as not to entrain air bubbles. The height of the liquid meniscus (i.e., distance between the top of the swollen gel layer and the meniscus of the liquid above it) in centimeters (h) is measured and recorded. The time needed for one centimeter of the saline liquid to drain through the gel ($\Delta t$) is measured and recorded in seconds. This value may be obtained by measuring the time required for the observed height of the meniscus in the cylinder to drop by 1 cm. Each sample is measured in triplicate. Values for SAP gel layer permeability are reported in units of $10^{-9}$ cm$^2$.

$$SAP \text{ Gel Permeability } (K) = (0.01 \times L) / [(980) \times (\Delta t) \times (h)] \quad \text{[Equation (2)], where:}$$

K=Gel layer permeability in $10^{-9}$ cm$^2$
L=Height of swollen gel in cm
$\Delta t$=Time in seconds
h=Height of the liquid meniscus in cm. In following Table 1 are values for CRC, AUL and gel permeability of the SAP samples

TABLE 1

CRC, AUL and Gel Permeability of the SAP samples

| Sample ID | CRC (g/g) | 0.3 psi AUL (g/g) | Gel Permeability ($10^{-9}$ cm$^2$) |
|---|---|---|---|
| Polymer A | 34.3 | 31.6 | 29.6 |
| Polymer A with 0.5% Aerosil R972 | 33.9 | 24.3 | 121.1 |
| Polymer A with 6% Aluminum solution | 31.2 | 24.8 | 326.2 |

Preparation of Froth and Foam

A polyolefin-based froth useful in preparing foam that may be fabricated into microcavitied foam structure embodiments of the invention, may generally be prepared as described in Published PCT Patent Application No. WO2005/021622 A2, 10 Mar. 2005, from dispersions of suitable olefin polymer particles, which teaching is specifically incorporated here by reference.

Dispersion Step

An aqueous dispersion of a selected polymer or polymers is suitably prepared by adding the polymer and the selected dispersant(s) in the desired amounts, and in a metered fashion, to the hopper of a bi-axial, polymer extruder where they are melt-kneaded at a temperature of about 220° C. (about 430° F.). Preferably, a long chain fatty acid of greater than 18 carbon atoms is melt-kneaded with the polymer. Then deionized water and base (e.g., KOH) sufficient to form in situ the fatty acid salt of dispersant, are added at about 150-165° C. (~300-330° F.) to the melt under a pressure of at least about 28 atmospheres (~2,800 kPa) to produce the dispersion.

Pressure within the extruder barrel is maintained above the saturated steam pressure of roughly 20 to 35 atmospheres (~2,000 to ~3,500 kPa) to avoid "blowback" through space between the barrel and screw of the extruder, by ensuring that space is essentially full of the dispersion. Then the dispersion is diluted with deionized water at a separate port downstream in the extruder barrel at about 193° C. (~380° F.) and at about 14 atmospheres (~1,400 kPa) to produce a final dispersion of about 50-60 percent solids. The dispersion is conducted from the extruder and collected, after passing through a mild cooling zone to prevent flashing of the water from the dispersion, at a temperature of about 95° C. (~200° F.).

Dispersion 1

Dispersion 1 represents an aqueous dispersion, made of AFFINITY™ 8200 polyethylene (available from The Dow Chemical Company, USA). This is an ethylene/1-octene copolymer of comonomer content 62/38 percent, having a density of 0.870 g/cm$^3$ and a melt index of 5 g/10 min by ASTM D1238 (190° C./2.16 kg).

Dispersion 1 comprises the noted ethylene/1-octene copolymer dispersed in an aqueous medium containing 3% of INDUSTRENE™ 106 dispersant (Witco Chemicals).

In the manner described earlier under the heading "Dispersion Step", 10,000 parts of the copolymer are fed into the hopper of a polymer extruder together with 640 parts (active weight) of dispersant (INDUSTRENE 106) and melt-kneaded by a single screw extruder at about 220° C. Downstream, into the barrel of the twin-screw extruder 70 parts potassium hydroxide in 850 parts deionized water are added to the polymer/dispersant blend under super atmospheric back-pressure at a temperature of about 155° C. As the blend passes down the extruder barrel, more deionized water is added until a final dispersion having about 56% polymer solids content is produced, as shown in Table 1, which is cooled to about 93° C. before exiting the extruder and is then recovered.

Dispersion 2

Dispersion 2 represents a dispersion of the previously noted AFFINITY 8200 copolymer that contains 2 wt % UNICID™ 350 dispersant (Baker-Petrolite) and 2 wt % HYSTRENE™ 4516 dispersant (Witco Chemicals). Dispersion 2 is prepared in the same way as described above for Dispersion 1, except that the dispersants used are UNICID 350 and HYSTRENE 4516 instead of INDUSTRENE 106.

Dispersion 3 (Dispersion Mixture)

A mixture of Dispersion 1 and Dispersion 2 is prepared by physical mixing. Varying amounts of Dispersion 1 are mixed with Dispersion 2 to give Dispersion 3 of the desired mixture ratio.

Dispersion 4

A fourth dispersion is prepared in the same way as described above for Dispersion 1 and Dispersion 2. Dispersion 4 contains the same final amount and types of dispersants as in Dispersion 3, but is made from a blend of Dispersions 1 and 2 in a 50/50 ratio.

Dispersion 5

Dispersion 5 is prepared so that the final amount and types of dispersants is 2 weight percent UNICID™ 350 dispersant, 1 weight percent HYSTRENE™ 4516 dispersant and 1 weight percent STEPANOL™ WAT-K dispersant.
Various dispersions and their compositions and properties are given in Table 2.

TABLE 2

Various Dispersions and their Compositions

| Sample Identity | Polymer | Dispersant(s) | Dispersant Conc. (wt %) | Particle ave. size (μm) | Solids (wt. %) |
|---|---|---|---|---|---|
| Dispersion 1 | AFFINITY ™ 8200 | INDUSTRENE ™ 106 | 3.0 | 2.04 | 55.9 |
| Dispersion 2 | AFFINITY ™ 8200 | UNICID ™ 350/ HYSTRENE ™ 4516 | 2.0/2.0 | 2.01 | 55.9 |
| Dispersion 4 | AFFINITY ™ 8200 | UNICID ™ 350/ HYSTRENE ™ 4516/ INDUSTRENE ™ 106 | 1.0/1.0/1.5 | 1.81 | 53.3 |
| Dispersion 5 | AFFINITY ™ 8200 | UNICID ™ 350/ HYSTRENE ™ 4516/ STEPANOL ™ WAT-K | 2.0/1.0/1.0 | 1.77 | 51.7 |

Froth Preparation Step

Suitably froth is prepared from an aqueous dispersion of the particulate thermoplastic polymer, obtainable as noted above, by using a high shear, mechanical mixing process to entrain air or another gas in the aqueous phase of the dispersion. The amount of air or other gas (where a gas in addition to or other than air is desirable) to be incorporated in the froth suitably comprises at least 80, preferably at least 85, and more preferably at least 90 percent by volume of the resultant froth. In general, all components to be used in making the froth are mixed together with mild agitation to avoid entrapping air. Once all of the ingredients are well mixed, the composition is exposed to high shear mechanical mixing. During this step the bulk viscosity increases as more air is entrapped within the continuous aqueous phase. The mixture is mixed until a non-flowable, stiff froth is formed. This generally produces a froth with density of less than about 100 g/L. The time to reach this stage varies with amount and type of frothing surfactant and the amount of mechanical shear. Any mechanical mixing device capable of whipping air into a thickened aqueous dispersion, such as a kitchen blender/hand mixer, Hobart mixer fitted with a wire whip or on a larger scale a Cowie-Riding Twin Foamer (Cowie Riding Ltd., G.B Patent 1,390,180). The commercial foamers also allow one to inject air into their high shear mixing head to obtain very low (less than 50 g/L) density froth. The frothing process may take place under any conditions as described above, for example, the frothing process may take place below the melting point of the thermoplastic polymer or at room temperature, e.g. 25° C.±10° C. The froth may have any viscosity as described above; for example, the froth may have a viscosity of less than 50,000 centipoises. All individual values and subranges less than 50,000 centipoises are included herein and disclosed herein; for example, the froth may have a viscosity of less than 30,000 centipoises; or in the alternative, the froth may have a viscosity of less than 20,000 centipoises.

Froth Preparation Method 1

A froth without fibers or additives is prepared from an aqueous dispersion of the polymer by using a household kitchen blender, for example, a stand mixer KitchenAid Professional mixer (Model KSM50) fitted with a wire whip.

A sample of 125 parts of any of the above-described dispersions is blended, for 30 seconds at a slow stirring rate (speed setting one on the blender), in a conventional mixing bowl with 11.5 parts of a 2% aqueous solution of a hydroxyalkyl cellulose ether, for example METHOCEL™ E4M hydroxypropyl methylcellulose supplied by The Dow Chemical Company. After the initial blend is prepared, the mixer speed is increased to the speed setting ten over a period of approximately 1 to 3 seconds, and at that speed whipping is then continued for another two minutes. A white froth is formed, which is non-flowable, stiff and easily handled.

Froth Preparation Method 2

A froth containing fibers is prepared using basically the same technique described above in froth preparation Method 1. After an initial blending of the particulate polymer dispersion and METHOCEL™ E4M, the desired amount of fibers selected from either polypropylene ("PP") fibers of 3 mm or 6 mm length (AL-Adhesive-C fiber which has a polypropylene core with a polyethylene sheath and is supplied by FiberVision) or a cellulose pulp fiber (supplied by Buckeye Foley) is added at a low stirring rate (speed setting two) over a time period of approximately 5-10 seconds, and the mixture is stirred for another 30 seconds. Then, as described above, the mixer speed is increased to speed setting ten over a period of approximately 1-3 seconds, and the whipping is continued for another two minutes. Typically, a white froth is formed which is non-flowable, stiff and easily handled.

Froth Preparation Method 3

A froth, with one or more of the selected organic or inorganic particulate additives noted earlier (such as, for example, zeolites, silicates, clays, etc.), is prepared using basically the same froth preparation procedure used in froth preparation Method 1 above. After initial blending of polymer dispersion and METHOCEL™ E4M, the desired amount of the powdered additive(s) is added at a low stirring rate (speed setting two) over a time period of approximately 5-10 seconds, and stirring the mixture is continued for another 30 seconds. Then, the mixer speed is increased to speed setting ten over a period of approximately 1-3 seconds, and whipping is continued for another two minutes.

Foam Drying Step

Suitably, drying of the aqueous polymer froth to form the desired resilient, polymer foam may be conducted in batch or continuous mode. Devices such as conventional forced air drying ovens or banks of infrared heating lamps or dielectric heating devices, e.g., radio, typically operated at permitted frequency bands in the range between 1-100 megaHertz, and microwave, typically operated at permitted frequency bands in the range between 400 to 2500 megaHertz, frequency energy generating sources, lining a tunnel or chamber in which the froth may be placed or conveyed through, in a continuous fashion, may suitably be employed for drying. A combination of such drying energy sources may suitably be employed, simultaneously or sequentially applied, to dry froth to form foam. The simultaneous use of a dielectric device and a forced air drying oven is a preferred mode of operation, and for foam on the order of a quarter inch (~0.6 cm) thickness the drying can be achieved as quickly as 45-90 seconds when the forced air oven is operated at approximately 75 deg C. and a radio frequency generator heats the froth to an internal temperature of about 45-50 deg C. The temperature of the drying operation is selected according to the nature and the melting range of the polymer, as determined by DSC, employed to prepare the foam, as described immediately below. The dielectric heating frequency bands, permitted for industrial use in various countries, are designated in greater detail in the reference "Foundations of Industrial Applications of Microware and Radio Frequency Fields", Rousy, G and Pierce, J. A. (1995).

Drying and Recovery Steps

Foam is suitably prepared by removing the liquid/aqueous element of a froth prepared in the manner previously described. Desirably, the amount of froth volume collapse during this conversion is to be minimized. Desirably, foam will have volume losses of not greater than about 30%, preferably less than about 10% and more preferably less than about 5% during the drying process. The froths are dried and converted to invention foams suitably by heating them in a forced air drying oven, at temperatures selected for optimum drying. Typically, for a froth made from a dispersion of an ethylene interpolymer, the froth is heated to a temperature between about 60 and 120° C. (~140 and 250° F.). As the nature of the thermoplastic polymer permits, processing is conducted at the highest temperature feasible to remove water as rapidly as possible from the froth without destroying the viscosity of the polymer on the surface of the bubbles of the froth or causing significant (e.g., more than 30 volume percent) collapse of the partially dried froth. Typically, it is desirable to perform the drying step at a temperature that approaches, but does not exceed the thermoplastic polymer's melting range, as defined below. The desired condition is to attain a temperature where the amorphous regions in the polymer can begin to coalesce while the pseudo-crosslinkings in the polymer, created by the crystalline regions in same, are still capable of imparting sufficient viscosity to the heated polymer to avoid or at least minimize froth collapse before the foam has become fully set or "dried" in its ultimate form and dimension and, as such, typically at least 95 weight percent of the water in the froth has been driven out.

The "melting range" of a thermoplastic polymer is determined by standard Differential Scanning Calorimetry (DSC) techniques. The temperatures that bracket the region of the DSC endotherm, or of the final endotherm if more than one endotherm exists, immediately before a return to baseline on the DSC scan plot determines the temperature range in which drying of the froth to form the finished foam is most suitably to be conducted.

The particularly preferred polymers, when used without other polymers or additives, are characterized by exhibiting a specific desirable DSC plot of their endotherm(s). In such polymers, the desired endotherm exhibits a relatively gradual positive slope as the scanning temperature is increased past the final endotherm maximum (i.e. the last inflection point, as represented by point A on the curve in FIG. 1, on a DSC curve where the curve slope then becomes positive and the curve returns to baseline state). This reflects a polymer of broad melting range rather than a polymer having what is generally considered to be a sharp melting point. Consequently, the drying temperature for a polymer is best maintained at or near a point (e.g., represented by point B on FIG. 1) on the endotherm curve a significant distance from the return to baseline position at which point a major part, but not all, of the crystalline portions the polymer fuse and polymer particles fuse or coalesce. During the drying process, by maintaining such a temperature, most of the polymer is allowed to fuse without a complete loss of polymer tensile strength and the bubble collapse that would otherwise ensue, if all crystalline portions of the polymer were to be melted quickly.

When drying is to be conducted with a dielectric heating source (e.g., microwave generator), it is desirable to ensure that the liquid used to provide the aqueous element of a froth contains at least a trace amount of ionic material. This can be accomplished by use of an ionic surfactant as the dispersant or frothing surfactant or by adding a small amount (e.g., 100 ppm) of water soluble alkali metal electrolyte salts, such as sodium acetate, potassium bicarbonate or the like, to the dispersion prior to or during frothing.

When a blend of polymer with additives, including blends with other thermoformable polymers, is to be employed in the preparation of froth and foam, a DSC plot for the blend is first suitably generated. From that plot endotherm(s) of the blend may be observed and, consequently, the final melting range of the blend determined and a suitable drying temperature for converting the froth to resilient foam can be selected.

In a preferred method for making foam, froth is continuously doctored onto a conveyor device from which the resultant foam will be recovered. Alternatively, a selected substrate is applied to the flat surface of the froth while it is in a mold and the froth, when dried, adheres to the substrate to form a laminated structure. On one side of the laminate is to be found the substrate and on the other side, the resultant foam with the microcavitied surface facing outward after removal from the mold. If desired, multiple layers of foam, separated by one or more substrate elements may be readily fabricated by alternating foam/substrate/foam/substrate, etc. As a matter of choice, the foam provides at least one outer layer of the laminate structure, with the molded microcavity-containing surface of the foam facing outward so it may then be loaded with particles selected for the foam's intended end use. However, the foam typically can be attached to a desired substrate in any conventional or convenient manner, e.g., by mechanical means, by use of adhesives, by heat lamination, etc., as can readily be perceived, selected and carried out by the artisan, in a manner to permit the molded microcavity-containing surface to be loaded with the selected particles.

In a preferred method, the froth is doctored on a mold atop a continuously moving conveyer and the drying step is conducted in a continuous rather than batch fashion. More preferably the drying step employs at least two energy sources, and which even more preferably are applied in a continuous fashion. Most preferably the at least two energy sources are configured in a manner to allow drying to be conducted either through a simultaneous or a sequential exposure of the froth to those drying energy sources.

A particularly preferred embodiment of the invention is to continuously doctor froth onto a mold and then to the Major Surface of the froth layer opposite the molded side of the froth, to continuously contact the froth with a substrate, which itself has fluid absorptive properties and to which the polymer in the froth may readily bond when heated. Drying then yields a laminated foam structure that creates a cohesive structure comprising two layers of different absorbent materials. A laminate structure with different wicking and/or fluid absorbent capacity properties in each laminate layer is thereby formed from which useful absorbent articles can be fabricated. For example a pre-formed, thermoplastic polymeric foam substrate layer of desired open-cell structure and desired cell size may serve as such a base substrate. Such a substrate layer is preferably made up primarily of the same thermoplastic material as that of which the froth is mainly comprised.

In the most preferred embodiment of the invention, a froth is continuously doctored onto either a mesh belt or a base substrate, such as a nonwoven or other foam layer, that rides on the belt. The belt carries the froth layer, or a composite of at least one froth layer, into a two stage drying apparatus/process that comprises both a convection heat and dielectric energy source to which the froth layer is subjected, in order to dry it. For a doctored froth thickness that is about 1 mm or less, a single stage convection heat dryer may suitably be used to dry the froth layer.

When the dry foam emerges from the drying segment of the continuous process, it is subjected to a thermal embossment step by introduction into a embossing apparatus, for example a heated pattern roller that thermally embosses the microcavities onto the foam surface or surfaces which it contacts.

One other means to obtain such a two-layer structure is to prepare a first froth of the invention, mold and dry it into a resulting foam and shape appropriately for use as a first substrate layer. Then upon that first foam substrate, lay down a second (same or different than the first) froth of the invention and dry the second froth to form the second foam layer. Alternatively, two froths are prepared and the first froth is prepared with a sufficient vertical compressive strength, so that the second froth can be laid on top of the first froth layer, which has been doctored onto a mold, without a significant reduction in the volume of the first froth layer.

One means to attain sufficient vertical compressive strength in the first froth layer is to select a first froth having a density greater than that of the second froth layer to be laid on it. Another means to attain the desired vertical compressive strength is to partially dry the exposed major surface of the first froth layer only enough to produce a light skin sufficient to support the weight of the second froth layer to be applied onto the first froth layer without significant reduction in volume of the first froth layer. Both froth layers are then simultaneously fully dried to foam, resulting in a two-layer foam laminate structure.

In another variant of the invention, a second foam layer is prepared from an extruded, open cell thermoplastic foam of a material of same or similar nature compatible to that employed in forming the first froth, and the first froth is laid on the second foam and the exposed Major Surface of the froth is then molded, and dried upon the second foam. Alternatively, the second foam layer is prepared from a different yet compatible type of open cell foam (e.g., a polyurethane open cell foam) then a layer of first froth (e.g., the aqueous polyolefin, open cell froth) is laid upon that second foam, the exposed Major Surface of that froth then molded and dried, to yield a useful dual layer foam structure.

In any of the structured, laminate embodiments of the invention, two different layers of foam having structures of differentiated capillary force, for example two different cell architectures or foams of different average cell sizes, are preferably selected for the first and second foams of a laminate structure. Because of the similar or same nature of the polymer base in the foam layers, a good bond is formed between them so that a structured laminate is formed which can exhibit a selected absorption and/or wicking property in each layer of the structure due to the different capillary force of the foam in each layer.

A foam with different cell architectures within it is one preferred embodiment of a structure exhibiting differentiated capillary forces. Such a structure provides a differentiated absorption and/or wicking capability in distinct layers of the structure. The polyolefin/polyurethane dual layer foam structure noted above, is one example of such a differentiated cell architecture.

Another embodiment, especially preferred, is a foam that has a major portion of substantially ellipsoidal cells, and having their major axis generally aligned in parallel fashion to a Major Surface, and lying in an xy-plane, of the foam. Such foam may be prepared by subjecting the microcavities-containing, resilient foam to mild heating while uniformly applying pressure to at least one surface of the foam in a cell orienting fashion. Preferably the major portion of the surface cells in the resultant foam become stably formed in a generally ellipsoidal shape, the major axis of such ellipsoidal cells being generally aligned with the xy-plane and roughly parallel to a Major Surface of the foam.

One method to achieve such ellipsoidal cell shaping and major axis orientation is to subject the resilient foam, preferably just after its drying, to a temperature at the lower end or at least substantially below the upper end of the melting range of its component polymer(s). The foam is heated to a temperature near the lower end of the melting range, providing sufficient heat to soften at least one surface of the foam without initiating foam collapse, while evenly and uniformly applying a modest pressure to that surface. Sufficient heat and pressure is applied to cause the diameter of such cells at least at and near such surface to be shortened along their z-axis, thereby causing them to assume the shape of a "flattened" beach-ball and imparting an ellipsoidal shape to those cells with the major (longest) axis of the three-dimensional cell oriented generally perpendicular to the z-axis and in an xy-plane of the foam. While cells below the surface of the foam to which pressure and heat is applied may also be "flattened" into ellipsoids, for may applications it may only be desirable to do so to the cells within a very limited distance from the foam's Major Surface; e.g., to a depth from that surface that represents a distance of 5-10% of the foams layer's total thickness.

In practice, for a polyethylene-based foam later described in preferred embodiments, the reorientation of cells into ellipsoidal shape is achieved by heating at least one surface to a temperature of from about 40 to about 100° C. while applying a suitable pressure. Such a typical suitable pressure (gauge) of from about 240 kPag to about 830 kPag (about 35 to about 120 psig) and preferably of between about 310 kPag to about 620 kPag (about 45 to about 90 psig) provides a foam with sufficient ellipsoidal cell structure at or near the surface to enhance the vertical wicking capabilities, over the same unmodified foam, several fold.

Drying Method 1

For the purposes of obtaining a suitable foam useful for testing, a froth prepared by any of the above-described preparation methods is spread onto household baking paper between two metal bars of a length of ca. 230 mm and a height of 6.35 mm or 3.18 mm and the froth is smoothed with a metal scraper to the height of the metal bar. The froth on the paper is placed in a Blue M forced air oven at the selected drying temperature of approximately 75° C. for 25 minutes. Normally, the resulting dry foam sheet is white and very soft.

Drying Method 2 (in-Mold Drying Process)

Froth prepared by any of the above-described preparation methods is spread on a mold (as shown in FIG. 2a) made of TEFLON™ fluoropolymer, aluminum metal or other suitable durable, smooth finish, machineable material of construction that bears a multiplicity of appropriately shaped microcavity-forming elements 230 within the body of the mold, to prepare a microcavitied foam structure. The froth is doctored into and smoothed with a metal scraper to the height of dd, as shown in FIG. 2c as 5 mm/0.197 in, of the mold over the microcavity forming elements (element 230, of height=dd minus ee, shown in FIG. 2c as 2.5 mm/0.98 in).

The mold suitably has one dimension that approximates or equals the desired width of the microcavitied foam absorbency structure to be constructed from the microcavitied foam and a second dimension that can approximate or equal the desired longitudinal dimension of such a structure, or may be longer than such desired dimension, later to be cropped or cut to the desired longitudinal dimension. For a continuous process, a mold constructed of a flexible material with an interior flexible release coating, such as a Teflon mold lining, may be desirable with such a mold mounted on a moving conveyor device of sufficient length to allow drying of the froth to the finished foam, stripping of the finished foam from the mold and return of the mold to the point of origin for repeated addition of froth.

Referring to FIG. 2b, in the mold embodiment to be utilized here, a mold is constructed from aluminum of dimensions aa=101.6 mm (4 in) by bb=355.6 mm (14 in) inside and cc=368.3 mm (14.5 in) outside the mold frame. The mold has a depth of 5.0 mm, and the micro-cylinders in the microcavities-forming side of the mold have a diameter of 3.0 mm and stand 2.5 mm high. The mold has two divisions, a flat mold, cavities-cover forming side, shown in FIG. 2a, element 210, and a microcavities-forming side, shown in FIG. 2a, element 220.

The mold, loaded with freshly formed froth, is placed in a Blue M forced air oven at the selected drying temperature of approximately 75° C. for 25 minutes. Then, the dry foam sheets both from the flat mold side and microcavitied mold side are recovered from the mold by softly peeling off by hand. Normally, white and very soft foams are obtained. In some cases, the molded dry foam sheets are so soft and/or friable that peeling them off is not possible without damaging and/or destroying the foam. The combined weight of the flat-side and microcavitied-side foams typically approximates 25 grams.

Drying Method 3 (Thin Foam Molding Process)

Froth prepared by any of the described methods is spread on a mold as previously described, except that the mold (not shown) lacks microcavity-forming elements and produces two flat, thin sheets of foam in its two flat-side mold divisions (each side akin to element 210 of FIG. 2a). The depth of the mold to be filled (and thus the thickness of the resulting foam), is 3.75 mm, inside the frame. The weight of the flat-side foam produced from the mold is approximately 11 grams, each side.

The mold loaded with froth is dried as described in the Drying Method 2, and then the dry thin foam sheets from both flat mold sides are recovered from the mold by softly peeling off by hand. This thinner foam is used as a top foam sheet and the microcavitied-side foam sheet (from Drying Method 2) is used as a bottom for the fabrication of a sandwiched composite pad. In some cases, the thinner foam from this mold is used as a top with another same thinner foam as a bottom foam sheet, for preparation of a sandwiched composite pad having no microcavities.

Drying Method 4 (Two Stage/Two Energy Source Drying)

In the continuous manner described above for the most preferred embodiment, using a two stage drying process employing a convection heat source and a dielectric energy (e.g., microwave) source, a first layer of a desired resilient foam made from a thermoplastic polymer (e.g., from an ethylene-based interpolymer) of a selected thickness is prepared and is subjected to a thermal embossment (thermoforming) step on a heated, pattern roller element having on its outer curved surface a design adapted to emboss a pattern of microcavities onto at least one, preferably major, surface of the foam as that foam passes under the roller surface under an appropriate compression pressure. The heated roller surface subjects the resilient foam to a temperature about 5-10° C. below its start of melting temperature, as determined by standard Differential Scanning Calorimetry methods. For example, foams of ethylene/1-octene copolymer similar to those foams described in the various embodiments, are suitably embossed at a temperature of between 75° C. and 95° C. and at a pressure of between about 35 kPa and 105 kPa (about 5 to 15 psi). In a parallel process, a thinner second layer of resilient foam made of a selected thermoplastic polymer, which may be the same or different polymer than that comprises the first foam layer, and without thermal embossment, i.e. thermoforming, of the thinner second layer. The two resulting foam layers are thereafter suitably joined after selected particles have been introduced into the microcavities of the first thicker foam layer, thereby constraining such particles in the microcavities of the resulting structure.

Preparation of Superabsorbent Polymer Composite Pad of Molded Foam

Irrespective of the above-described froth preparation and drying methods, when examined using a scanning electron microscope (SEM), the open-cell foams from Dispersions 1 through 4 exhibit cell size gradients from small cells on the outer surface to larger cells in the interior of each foam sheet sample. This result is desirable, especially in absorbent applications where the foam needs to take up a fluid quickly, yet also wick fluid quickly away from the contact surface of the foam toward the opposite surface.

In the present invention, the foams are used preferably in a sandwiched pad form. The sandwiched pad comprises a flat-side molded foam as top and a microcavitied-side mold foam as bottom. With either foam, the larger cells of the outer surface will be contacted first by an aqueous solution. Then, the capillary action of the cell size gradient created by increasingly smaller open cells in the direction toward the foam interior, will serve to wick the aqueous solution from the surface toward to the interior where SAP particles are located in the microcavities of the foam sandwich.

In the present invention, the foams are most preferably used as a sandwiched pad composite containing absorbent particles constrained between the thin, flat foam component and the microcavity-structured foam component. To prepare the composite structure, microcavitied foam is laid such that the openings of the microcavities are facing upwards. A stainless steel metal template that exactly matches the size and configuration of the microcavities is then placed over the foam sheet, and a measured amount of the particulate material, preferably SAP particles, is scraped through the template holes into the microcavities. Either a fine powder or a commercial SAP powder can be used, and examples are described earlier and designated Polymer A, B and C.

In the operative embodiments described below, size fractions smaller than approx. 315 microns (Polymer C), from approx. 100 to 500 microns (Polymer B) and from approx. 100 to 850 microns (Polymer A) are used. Unless otherwise noted, 12 grams of each Polymer type are used per foam pad. On one side of the foam sheet the microcavities 303, as seen in FIGS. 3 a-b, are able to accommodate approximately 20 grams (on a foam sheet of 10.16 cm (4 in) by 35.56 cm (14 in)) of Polymer particles 305 without being overfilled. After the microcavities are filled with SAP powder particles and other optional organic or inorganic particulate additives, borders around the foam sheet are spread thinly with Rubber Cement (ELMER'S™ Products Inc., USA) along approximately a 4 mm edge strip. Then a "sandwiched" foam pad is prepared by putting a flat-side foam sheet 310, as shown in FIGS. 3 a-b, onto the microcavitied-side sheet 301, as shown in FIGS. 3 a-b, so that the glue causes adherence along the border edge 4 mm strips (not shown in FIGS. 3 a-b). In all cases, the flat-side sheet and microcavitied-side sheet of foam are oriented so that cell size gradients range from small cells on the outer surface to larger cells in the interior of the sandwiched structure. The sandwiched, glued sheets are then after initial contact gently pressed together under the flat surface of a mold plate, for approximately 5 minutes, to complete cure of the glue.

Preparation of Composite Pads of Sap and Foam Via Thermal Embossment (Thermoforming) Process The polymer materials used in this invention are thermoplastics. Thermoplastics can be heated to there softening points and reshaped utilizing preshaped molds. These molds can be in form of a female cavity that utilizes vacuum to pull the softened thermoplastic into the mold with the resulting cooled formed specimen taking the shape of the mold. The mold may also be a male heated mold that is pressed into the thermoplastic foam thereby softening the foam that is in contact therewith and shaping into the shape of the mold. This may for example be done in a continuous process by utilizing a heated embossing roll. The laboratory method used for demonstrating this technology is explained hereinbelow.

Composite pad samples via thermal embossment, i.e. thermoforming, process are prepared, using Dispersion 5 and with Drying Method 1. The pad samples have a thickness of 3.18 mm and are cut to the size of 10.16 cm by 21.59 cm to fit inside the aluminum micro cavity mold. The cut specimen is placed on top of the male side of the mold and both are placed into the oven at 75° C. for 5 minutes. Immediately upon removal of the mold and specimen from the oven, a piece of STYROFOAM® brand insulation is placed on top of the foam and weights are placed on top of the STYROFOAM® for 5 minutes. The weights, STYROFOAM®, and froth foam are removed from the mold leaving thermoformed pockets in the froth foam.

To fill the thermoformed pockets a template is placed over the formed specimen. The template has a hole pattern drilled into it that is the same as the male microcavity mold. With the steel metal template in place 12 grams of dry Polymer A powder are sprinkled over the specimen and drop directly into the thermoformed pockets. A vibrating tool can also be used to help distribute the left over particles on the template.

To apply a covering over the filled thermoformed specimen another batch of froth is produced in the mixer (Froth Preparation Method 1). The specimen without Polymer A (control) and with Polymer A particles is laid flat and thickness bars (0.635 cm) are placed on each side. The froth foam is placed on the screening tool and then applied to the thermoformed specimen in a fluid continuous motion using the thickness bars on both sides as a guide. The specimen is then placed in an oven at 75° C. until dry for 25 minutes. A circular foam sample of 50 cm$^2$ area (diameter of 8.0 cm) is cut by punching out from each pad and is used for MTS liquid absorption testing.

Preparation of Compressed Foam

The sandwiched foam pad, with or without an SAP powder content, is wrapped with a thin Teflon imbued paper of thickness of 25 microns, and then compressed. The compression of the wrapped foam pad is conducted by pressing for 30 seconds or one minute ('heat compression'), using a Dake Hydraulic Press (model 44251). The Teflon imbued paper allows the compressed foam sheet to be easily peeled off the press and recovered. Typically, the sandwiched foam pad has a size of 10.16 cm (4 in) by 35.56 cm (14 in) and may be of varying initial thickness of from about 3.18 to 6.35 mm. The temperature and pressure preferably are varied from 55° C. to 100° C. and from 1 to 2 metric tons, respectively. Ambient humidity is maintained at about 50%, and thickness of the compressed foam pad by limiting the distance the press may travel. The shim size depends on the desired compressed pad thickness. In ambient temperature at approximately 22° C., shims are used to control the resulting a typical heat compression experiment, a set of shims having approximately a length of 23 cm is used. Shim thickness is varied from 0.0937 in (2.38 mm) to 0.180 in (4.57 mm). Pads are allowed to cool for approximately 5 minutes after pressing, at which time the compressed pad thickness is measured.

Perforation

In some cases, the compressed foam pads are perforated. Perforation of a foam sample is conducted on a rollable cone bearing 6.35 mm protruding spikes. Samples are rolled over by the cone with spikes going all the way through a sample until approximately 20 holes per square centimeter are created.

Foam Density (Dry Basis)

Length, width, and thickness is measured on a full size molded foam sample or a specimen cut from the molded sample. Thickness is measured under 0.05 psi (ca. 0.35 kPa) pressure. Dimensions are recorded and the sample or specimen is then weighed. Volume is calculated from the dimensions and divided into the weight of the foam sample. Units reported are grams per cubic centimeter (g/cm$^3$).

Visual Appearance

Samples are laid out and divided into three categories based on visual appearance. The three categories are: Smooth which has no surface blemish; Few Cracks which has surface cracks but not deep enough to hinder performance/physical properties significantly; and Large Cracks which are cracks deep enough to influence results of physical property testing.

Softness

Samples are laid out and classified into three categories based on the tester's judgment. The three groups are soft, medium, and firm. These classifications are only based on the sample population. Soft is a velvet feel and sample deforms at the slightest finger pressure; Medium is smooth and requires a small amount of pressure to deform the sample; and Firm is smooth or rough feeling and is stiff to finger pressure, hardly yielding at all to firm pressure.

Foam Permeability

Air permeability ($K_p$) of a sample is a measure of the air flow through the sample, relative to the sample thickness and pressure drop across the sample cross section A.

$$\text{Foam Permeability } K_p (Q \times \mu \times L)/(P \times A) \quad \text{[Equation (3)], where}$$

$K_p$=Permeability in darcies
Q=Air flow in cm$^3$/sec
A=Surface Area in cm$^2$
$\mu$=Viscosity of Air in cP
P=Pressure drop in atm
L=Thickness in cm.

Flow data is generated on TexTest Air Permeability Tester model FX3300. It is necessary, for reliable permeability results, that all points in a sample material have minimal variation in permeability for the material to have the same fluid flow efficiency throughout.

Foam Bending Modulus

This test measures the bending stiffness of a foam specimen by allowing a narrow strip of the foam to bend a fixed angle under its own weight. The length of the fabric required to bend to this angle is measured and is known as the bending length. The test specimens are each 25 mm wide and 200 mm long. The specimens are prepared and the test conducted as described in the test method for Shirley stiffness test in "Physical Testing of Textiles," pages 258-259; (Edited by B. P. Saville, CRC Press, Woodhead Publishing Limited, Cambridge England, reprinted 2000).

The stiffness of a foam strip is dependent on its thickness. The thicker the foam, the stiffer it is if all other factors remain the same. The bending modulus is independent of the dimensions of the strip tested. It is a measure of intrinsic stiffness and is given in Equation (4).

$$\text{Bending Modulus (in N/m}^2\text{)} = (12 \times G \times 10^3)/T \quad \text{[Equation (4)], where}$$

G=Flexural rigidity=$M \times C^3 \times 9.807 \times 10^{-6}$ (in μNm)
C=Bending length in cm
M=Foam strip mass per unit area in g/m$^2$
T=Foam thickness in mm.

Cradle Test for Back-Wetting, Intake and Wicking Length

Figure 4:
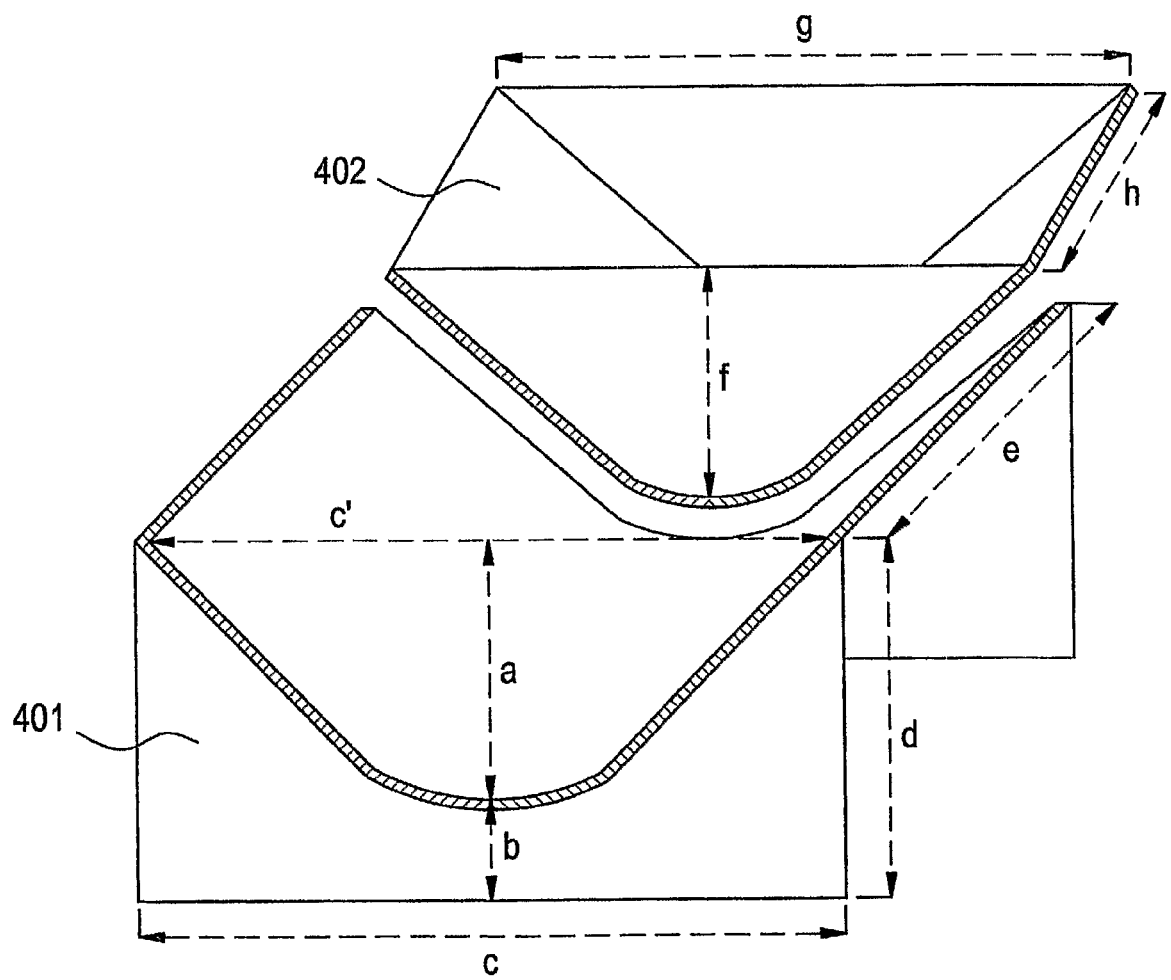
FIG. 4 illustrates a U-shaped apparatus for testing of an article or structure prepared from microcavity-structured foam.

Both abilities to quickly absorb a fluid and to diffuse it throughout a diaper are important features for the evaluation of a diaper's overall performance. The 'cradle test' is used to determine the performance of composite foam absorbency pads (hereafter 'pads') and of diapers containing composite pads of the present invention (hereafter, 'diapers') with regard to intake, back-wetting and wicking length. In order to get reasonably realistic data, diapers and pads are evaluated under pressure in a "cradle" test apparatus made of PLEXIGLAS™ or of other comparable acrylic plastic material. FIG. 4 illustrates an assembly of congruent U-shaped base and load-holder forms made of PLEXIGLAS™ that make up the cradle test apparatus. Element 401 is the base of the apparatus and element 402 is a load holder comprising a chamber adapted to hold within the "U" the desired weight to be applied in the test. Element 402 is of height f, width g and breadth h. Load holder 402 is designed to fit congruently into the U-shape formed by the base element 401 having a height a within the "U" shaped depression, an internal width c' from rim to rim and a breadth of e. The apparatus is designed so that height f is slightly greater than height a, while width g is slightly less than width c' and breadth h is appreciably less than breadth e. For example, their respective magnitude may be selected as follows. For element 401: a=8.0; b=3.4; c=21.4; c'=20.1; d=11.4; e=20.0; and for element 402: f=8.2; g=20.0; h=15.0, units.

Equipment and Test Liquid

Balance—accuracy 0.01 gram, METTLER™ Model 3600 or equivalent;
Two U-shaped forms made of PLEXIGLAS™, of FIG. 4 configuration;
A 4.2 kilogram weight made of metallic beads contained in a strong plastic bag;
Filter paper Whatman No. 1, diameter 12.5 cm;
Plastic disk (Plexiglas plate), 12.5 cm inner diameter;
Stainless steel load of 8.63 kg with diameter of 12.5 cm (yielding 1 psi or 6.9 kPa);
A 100 mL addition funnel;
A 100 mL graduated cylinder;
Timer—accurate to the nearest 0.1 s;
Aqueous 0.9% NaCl solution as test liquid; and
Blue dye, methylene blue (0.5% in 0.9% NaCl aqueous).

Sample Preparation of Diaper Chassis

The composite pad of the present invention was inserted into a commercially available diaper chassis for testing. The chassis employed for testing of the invention was a HUGGIES™ premium size 4-brand diaper, which was a commercial product of The Kimberly-Clark Company, USA.

The chassis was prepared by stretching out the commercial diaper on a table-top with the outside surface of the diaper (back sheet) facing upward, and onto each of the four edges of the diaper a weight of approximately 1 kg was placed. This helped to keep the diaper stretched and laying flat for better handling. Using a razor the diaper back sheet was cut roughly along the longer (median) diaper axis and then again for the breadth of the diaper and roughly perpendicular to the line of the median cut, once at each end of the length cut. The result was to open the diaper back sheet in the shape of an "I" cut. The diaper core composite, comprising basically cellulose fibers and superabsorbent polymer, was thoroughly removed from the diaper, and the bare diaper chassis was obtained.

A compressed foam composite pad made as described above was inserted into the chassis in place of the diaper core material removed, and then the cuts were fastened back together with transparent tape. The cuts were tightly closed so that there was no fluid leakage through the cuts.

Cradle Test Procedure

The addition funnel is placed on a ring stand, and then filled with 60 mL of the methylene blue dye/saline solution. The weight of the composite pad or diaper is recorded, and then the pad or diaper is centered in the U-shaped Plexiglas base member 401 of the cradle test apparatus described in FIG. 4, with the non-woven diaper portion or pad facing upward, as if it were being worn by a baby. In the case of diaper, the adhesive tabs can be flipped back out of the way.

The cradle form containing the pad or diaper is placed beneath the funnel so that the funnel opening is centered over the diaper approximately 13 cm above the top sheet. The funnel stopcock is fully opened and simultaneously the timer is started. The solution is added at approximately 7 mL/sec holding the funnel one inch (ca. 2.54 cm) from the face of the non-woven of the diaper or pad. The timer is stopped when all the excess liquid has soaked through the diaper top sheet. The elapsed time is recorded as the "first insult" intake time.

The second, smaller and conforming U-shaped load member 402 of the FIG. 4 test apparatus is placed on top of the diaper or pad then the 4.2 kg weight is applied for 10 minutes to remove excess liquid. Six filter papers are weighed and their weight is recorded as $W_0$. The U-shaped cradle load member 402 is removed and the diaper is lifted out, weighed, and laid flat. Onto each of the four edges of the diaper a weight of approximately 1 kg is placed to keep the diaper stretched. The filter papers and the Plexiglas disk of 12.5 cm diameter are placed together on the crotch area of the diaper. With the filter papers sandwiched between the Plexiglas disk and the diaper, an 8.63 kg weight is placed on the Plexiglas. After 1 minute the Plexiglas disk is removed and the wet filter paper is weighed and recorded as $W_1$. "Back-wetting" of the sample is expressed as $(W_1-W_0)$ in grams.

The "fluid extension" of a sample, observed as a wicking-length, is measured in centimeters. This measurement is an arithmetic average of the maximum and minimum fluid extension, observed along the diaper main (longitudinal) axis, from center of diaper. The sequence above is repeated, using 24 filter papers for each subsequent back-wetting measurement, after each of a $2^{nd}$ and $3^{rd}$ saline addition.

SAP Loading Test Procedure

The SAP loading test procedure is a process in which diapers with unknown amounts of superabsorbent polymer are tested against a known set of standards. An ion exchange that takes place between potassium ion and sodium ion is measured for this purpose. The SAP polymer is a polymeric carboxylic acid that is normally sold in its sodium salt form, and the sodium salt content is a known quantity, typically about 30%-50% of the total SAP dry weight. In testing a diaper for SAP loading, the diaper core is mixed well with a potassium chloride solution of known concentration, in a sufficient amount to provide an excess of potassium ion, so that potassium ions will replace all of the sodium ions. A sodium selective electrode is then used to determine the sodium ion concentration of the filtered solution. The mass of the SAP is determined by comparing the millivolt (mV) reading of the pH meter (ROSS™ Sodium Electrode, Model 84/86-11, Thermo Orion Inc., USA) with the calibration curve of mV readings of standard solutions for different SAP loadings of predetermined sodium content.

Ambient temperature for testing should be at approximately 22° C. with 50% relative humidity. The diaper is stretched out with weights so that the backside is facing upwards. Using a scalpel or other sharp instrument, the back of the diaper cut and opened in an "I form", and the diaper core is extracted manually. The diaper core is weighed and weight recorded. Core is placed in gallon jug with lid, and 3000 ml of KCl solution of known concentration are poured into jug. The mixture of KCl solution and extracted diaper core is stirred for 10 minutes. Then a large funnel is used to gravity filter the mixture. A nylon mesh of ca. 150 mesh is placed inside the barrel of the funnel to separate the SAP gel from the salt solution when filtering a sample. A 32-ounce (ca. 945 mL)jar with lid is used to contain the filtered solution. A water bath with a 150 mL glass jar with inlet and outlet openings that are connected to the water-bath is used to circulate water at a constant temperature of 30° C. around the sample cup. The sample cup is flushed with some amount of the intended sample and then 60 mL of sample are added. The sodium ion-specific electrode is inserted into the sample solution and after 5 minutes the mV reading is recorded. Data is compared to a set of known standards to give the amount in g of the SAP polymer in a sample. The amount of SAP in the diaper sample is evaluated in triplicate.

Dip-and-Drip Method

This diaper test method determines the total absorption capability of a diaper and is used to determine the performances of diapers.

A diaper is taken and weighed (initial weight). A large tray, of approximate volume of 300 mL, is filled with 2500 mL of aqueous 0.9% saline solution. The sample diaper is put into the tray with the saline solution and with the inside of the diaper facing upwards. A plastic panel is placed on top of the diaper to make sure the diaper is completely submerged beneath the saline solution. After thirty minutes, the plastic panel is removed, and the diaper is taken by its belt, and is hung on the bar with the diaper's polyethylene back-sheet layer against the bar to allow unabsorbed solution to drip away. After one minute, the diaper is taken down from the bar, and is placed in another tray and weighed ("drip weight").

By calculating the difference between drip weight and initial weight, the quantity of saline solution absorbed is obtained ("total absorption"). The total absorption is then further divided by the amount of the SAP present in the diaper sample to calculate the saline solution absorption per gram SAP. This parameter is a standard measure of the absorption capacity of the SAP polymer in the diaper.

MTS Liquid Absorption Method

This method, owned by Marketing Technology Service, Inc., measures how much liquid a core can absorb at various flow rates, how much is retained when pressure is applied and how much collapse occurs.

A 50 cm$^2$ sample (diameter of 8.0 cm) is used, and the sample is weighed and an initial thickness is taken to determine density and record initial thickness. In large beaker, of approximate volume of 3000 mL, is filled with 2500 ml of 0.9% saline solution. A testing stand, 45 cm tall, 28 cm wide and 23 cm deep is set up with a 1000 ml funnel with a 2.5 cm bottom opening set above a 1000 ml receiving beaker. A PG5002-S balance is placed under the testing stand to record how much liquid is run out of sample. This liquid amount is used to determine how much was absorbed into sample. Rulers are attached to the top of the stand to measure how much the sample swells or collapses.

A Masterflex LS pump model 77200-60 is used to dispense the testing solution at a rate of 100 ml in 14 seconds. Masterflex 6409-16 Tygon tubing is used to deliver the fluid from the testing solution through the pump into the sample using a 0.1 kpa (equals 0.0145 psi) spreader that is 8 cm in diameter and 0.5 cm thick and weighing 50.0 g is placed on top of the sample. A PE backing sheet is placed under the sample, on top of a screen on the testing stand to prevent fluid from passing directly though the sample and not wicking out though the sample. The zero of the rulers on top of the stand should be at the bottom of the sample. The sample is then insulted with the testing fluid. After 2 minutes the thickness of the sample is measured using the rulers on top of the stand. The amount of fluid that was captured in the receiving beaker is also recorded. A 3 kpa (0.435 psi) weight (diameter of 6.0 cm×height of 6.5 cm and weighing 1450.0 g) was then placed on top of the sample and 2 minutes later the thickness is again recorded and the run off is recorded. Finally another 2 pka (0.290 psi) weight (diameter of 6.0 cm×height of 4.5 cm and weighing 1000.0 g) is added and after 2 minutes the thickness and run off is recorded.

SPECIFIC EMBODIMENTS OF THE INVENTION

All reported percentages are by weight, unless otherwise stated.

Examples 1 through 10 demonstrate composites comprising superabsorbent polymer particles and a microcavity-structured, open-cell foam comprising a blend of an olefin polymer and a multiplicity of fibers as well as a Diaper containing the composites of the present invention. Examples also demonstrate the relative effectiveness of SAP particles with different particle sizes and surface treatment, as well as the various methods for incorporation of SAP particles into microcavities in a composite structure.

EXAMPLE 1

Composite Pads of SAP and Foam Made from Dispersion 1 Using Drying Method 1

Foam samples are prepared for bottom pads, using Dispersion 1 and with Drying Method 1. The foam samples have a thickness of 6.35 mm or 3.18 mm and are cut to the size of 10.16 cm by 21.59 cm. Then 7.68 grams of Polymer B are distributed onto the flat bottom pad by spreading through the stainless steel template. On the top of the resulting SAP micro-islands is placed a three-dimensional, open-cell polypropylene foam sheet having a thickness of approx. 150 microns of the same dimensions as the foam pads (3.18 mm and 6.35 mm Pad in Table 3). In one experiment, a thin polypropylene fiber mat is inserted onto the polypropylene sheet (6.35 mm "Pad with fiber mat" in Table 3). The thin layer of fiber mat is prepared by spreading about 1 gram of 6 mm polypropylene fibers (AL-Adhesive-C FIBERVISION™ polypropylene fiber of 6 mm length). The FIBERVISION™ fiber is spread on the Teflon cloth in an approximate size of 10.16 cm by 21.59 cm, wrapped with Teflon imbued paper, and then heat compressed under 2 metric tons (MT) pressure at 75° C. for one minute, without shims.

The sandwiched foam pads with SAP micro-islands in the middle layer are compressed under 2 MT pressure at 75° C. for one minute, using shims of 3.18 mm thickness. The samples are subjected to the cradle test for intake, back-wetting and wicking length. The results are summarized in Table 3.

TABLE 3

Pad Experiments with Foam Containing SAP

| | Sample Identity | 3.18 mm Pad | 6.35 mm Pad | 6.35 mm Pad w/ fiber mat |
|---|---|---|---|---|
| Intake (sec) | $1^{st}$ Insult | 45.5 | 60.6 | 42.2 |
| | $2^{nd}$ Insult | 59.2 | 112.0 | 60.3 |
| | $3^{rd}$ Insult | 153.3 | 117.3 | 122.4 |
| Back-wetting (g) | $1^{st}$ Insult | 0.4 | 0.4 | 0.5 |
| | $2^{nd}$ Insult | 2.2 | 2.3 | 1.7 |
| | $3^{rd}$ Insult | 10.0 | 7.2 | 6.6 |
| Wicking-Length (cm) | $1^{st}$ Insult | 15.5 | 14 | 13 |
| | $2^{nd}$ Insult | 18 | 16 | 15 |
| | $3^{rd}$ Insult | 21 | 18 | 17 |

The 6.35 mm pad shows a slower intake and shorter wicking length and a slightly better back-wetting than the 3.18 mm pad. A fiber mat inserted into the 3.18 mm composite pad to make a 6.35 mm pad, improves the intake time and back-wetting over the 6.35 mm pad without a fiber mat.

EXAMPLE 2

SAP Fines/Foams Composite Pads Made from Dispersion 1 Using Drying Method 1

Foam samples were prepared, using Dispersion 1 and with Drying Method 1. The foams had a thickness of 3.18 mm and were cut to the size of 10.16 cm by 21.59 cm. Non-surface treated SAP fines or surface treated SAP fines (Polymer C) (7.68 grams) were distributed onto the bottom pad by spreading through the stainless steel template onto the foam surface having no microcavities. On the top of the resulting SAP micro-islands was placed a three-dimensional open-cell polypropylene foam sheet having a thickness of approximately 150 microns of the same length and width as the foam pad. The sandwiched foam pads with SAP micro-islands in the middle layer were compressed under 2 MT pressure at 75° C. for one minute, using shims of a thickness of 3.18 mm. The samples were subjected to the cradle test for intake, back-wetting and wicking length. The results are summarized in Table 4.

TABLE 4

Pad Experiments with Foam Containing SAP Fines

| | Sample Identity | 3.18 mm Pad with Non-Surface treated Fines | 3.18 mm Pad with Surface Treated Fines |
|---|---|---|---|
| Intake (sec) | $1^{st}$ Insult | Gel Blocking | 148.8 |
| | $2^{nd}$ Insult | N/A | 260.7 |
| | $3^{rd}$ Insult | N/A | 318.4 |
| Back-wetting (g) | $1^{st}$ Insult | Gel Blocking | 1.0 |
| | $2^{nd}$ Insult | N/A | 2.4 |
| | $3^{rd}$ Insult | N/A | 4.3 |
| Wicking-Length (cm) | $1^{st}$ Insult | Gel Blocking | 16 |
| | $2^{nd}$ Insult | N/A | 17 |
| | $3^{rd}$ Insult | N/A | 18 |

N/A = not applicable

The 3.18 mm pad with the non-surface treated fines SAP in Table 4 showed no absorption due to the gel blocking. The liquid of the first insult in the cradle remained unchanged and unabsorbed, even after 20 minutes. The test was stopped. The pad with the fumed silica particles-surface treated fines (Polymer C) showed different performances. Gel blocking was not seen. The intake was somewhat slower than that for the 3.18 mm pad sample with Polymer B in Example 1. However, back-wetting data showed a better value than, and wicking data similar to, the 3.18 mm pad in Example 1.

EXAMPLE 3

Effects of Mixture of Dispersions 1 and 2 on Foam Quality

Dispersion 3 of various mixing ratios between Dispersion 1 and Dispersion 2 was prepared using Drying Method 2 with a Teflon mold. The results for density, permeability, visual appearance as well as softness of the dry foams are summarized in Table 5.

Foams made 100% from Dispersion 2 are very soft and show few cracks. However, these foams are so soft and friable that peeling off the foam from the microcavitied-side mold is difficult and results in damaged foams. Foam made 100% from Dispersion 1 in general shows a visual appearance with large cracks and a firm feel. The mixture of Dispersion 1 and Dispersion 2, ranging from 25% to 50% of Dispersion 2 shows improved softness and visual appearance with reduced or absent cracking.

EXAMPLE 4

Compression Experiments and Effects of Fibers and Temperatures

The foams were prepared by Froth Preparation Method 2 using different mixing ratio between Dispersion 1 and Dispersion 2 and using Drying Method 2 in a Teflon mold. Fibers of different types and amounts were incorporated into dispersions. The molded foams were put into a sandwiched foam pad and the pad, without any SAP powder, was then compressed. Compression was conducted with a set of shims having a thickness of 4.32 mm for a compression time of 30 or 60 seconds. The temperature and pressure were varied from 55° C. to 75° C. and from 1 to 2 metric tons, respectively. The results for the pads obtained from the compression operation are shown in Table 6, which includes the foam qualities of softness, visual appearance and density, as well as permeability.

It is clear, as seen in Table 6, that a 50/50 mixture of Dispersion 1 and Dispersion 2 with 1 g of PP fiber having 3 mm length gives very good foam quality. For example, flexible, soft and uncracked as well as more permeable foams are created even after the compression process. In some cases, a rather high density foam is obtained when an amount of 4% fibers is used. This finding is attributed to a partial collapse of the frothed foam. It is interesting to note that the compressed foams from the 50/50 percent mixture also exhibit higher permeability than the other foams. In all cases, the foams in Table 6 show no cracks. In particular, a mixture ratio of 50/50 percent of Dispersion 1 and Dispersion 2 results in softer foams even after compression than Dispersions 1 and 2 alone or than a 75/25 percent mixture of Dispersion 1 and Dispersion 2.

EXAMPLE 5

Dispersion 4 and Foam Quality

Foams were prepared with Dispersion 4 which contained the same final amounts and types of dispersants as in Dispersion 3 with a 50/50 percent mixture ratio. The properties of Dispersion 4 are given in Table 7.

In general, foams were so friable that peeling the foams off the mold resulted in some damage to the foams. Large cracks, that were seen both in the Teflon and Aluminum molded foams without fibers, were greatly improved by addition of fibers but cracks were still present after one percent PP (3 mm) fibers were added to the foam. This surprising finding strongly suggests that the results seen in Table 5 and Table 6, with regard to the 50/50 percent mixture effect of Dispersion 1 and Dispersion 2, are not seen with Dispersion 4, which has the same final dispersant concentration.

EXAMPLE 6

Effects of Fibers on Foam Quality

Different amounts of PP fiber, 3 mm in length, were incorporated into Dispersion 1 or Dispersion 2 or a mixture of different ratios of Dispersion 1 and Dispersion 2 and were dried by Drying Method 2. The results for flat-side foam and microcavitied-side foam (i.e., from the respective mold side) are seen in Tables 8 and 9, respectively.

Irrespective of the mold type, most of the foam sheet samples in Tables 8 and 9 exhibit soft and very smooth surfaces without cracks. Due to the microcavities, the density of the microcavitied-side foams (Table 9) was lower than the flat-side foams (Table 8), and significantly more flexible, that was the bending modulus was significantly lower. The mixture of Dispersions 1 and 2 (where Dispersion 2 ranges between approximately 30 to 75 percent) showed good flexibility and softness and a lower degree of cracks. A 50/50 mixture showed surprisingly good overall properties with regard to flexibility, visual appearance, and softness.

TABLE 5

Non-Compressed, Non-Fiber Containing Flat-Side Molded Foam from Teflon Mold by Drying Method 2

| | % Dispersion | | Density | Permeability | Visual Appearance | | | Softness | | |
|---|---|---|---|---|---|---|---|---|---|---|
| Sample ID | Dispersion 1 | Dispersion 2 | (g/cm3) | (Darcy) | Smooth | Few Cracks | Large Cracks | Soft | Medium | Firm |
| 5-1 | 0% | 100% | 0.055 | 286 | | X | | X | | |
| 5-2 | 50% | 50% | 0.096 | 216 | X | | | X | | |
| 5-3 | 65% | 35% | 0.086 | 251 | X | | | X | | |
| 5-4 | 75% | 25% | 0.075 | 325 | | X | | | X | |
| 5-5 | 80% | 20% | 0.075 | 288 | | | X | | | X |
| 5-6 | 100% | 0% | 0.061 | 110 | | | X | | | X |

TABLE 6

Compressed, Fiber Containing Sandwiched Foam Pad from Teflon Mold by Drying Method 2

| | % Dispersion | | | Compression | | | Density | Permeability | Visual Appearance | | | Softness | | |
|---|---|---|---|---|---|---|---|---|---|---|---|---|---|---|
| Sample ID | Dispersion 1 | Dispersion 2 | % Fiber* | Temp deg C. | MT | Time | (g/cm³) | (Darcy) | Smooth | Few Cracks | Large Cracks | Soft | Medium | Firm |
| 6-1 | 0% | 100% | 4% CF | 75 | 2T | 60 sec | 0.199 | 31 | X | | | | | X |
| 6-2 | 0% | 100% | 4% PP 3 mm | 75 | 2T | 60 sec | 0.182 | 26 | X | | | | | X |
| 6-3 | 50% | 50% | 4% PP 3 mm | 65 | 2T | 30 sec | 0.171 | 38 | X | | | | | X |
| 6-4 | 50% | 50% | 1% PP 3 mm | 65 | 1T | 60 sec | 0.159 | 92 | X | | | | X | |
| 6-5 | 50% | 50% | 1% PP 3 mm | 65 | 2T | 30 sec | 0.151 | 108 | X | | | | X | |
| 6-6 | 50% | 50% | 1% PP 3 mm | 60 | 2T | 30 sec | 0.164 | 90 | X | | | | X | |
| 6-7 | 50% | 50% | 1% PP 3 mm | 55 | 2T | 60 sec | 0.169 | 78 | X | | | | | X |
| 6-8 | 75% | 25% | 4% CF | 75 | 2T | 60 sec | 0.303 | 23 | X | | | | | X |
| 6-9 | 75% | 25% | 4% PP 3 mm | 65 | 2T | 30 sec | 0.177 | 55 | X | | | | | X |

TABLE 6-continued

Compressed, Fiber Containing Sandwiched Foam Pad from Teflon Mold by Drying Method 2

| Sample ID | % Dispersion | | % Fiber* | Compression Temp deg C. | MT | Time | Density (g/cm³) | Permeability (Darcy) | Visual Appearance | | | Softness | | |
|---|---|---|---|---|---|---|---|---|---|---|---|---|---|---|
| | Dispersion 1 | Dispersion 2 | | | | | | | Smooth | Few Cracks | Large Cracks | Soft | Medium | Firm |
| 6-10 | 75% | 25% | 4% PP 3 mm | 60 | 2T | 30 sec | 0.172 | 44 | X | | | | | X |
| 6-11 | 75% | 25% | 4% PP 3 mm | 55 | 2T | 30 sec | 0.193 | 35 | X | | | | | X |
| 6-12 | 75% | 25% | 1% PP 3 mm | 65 | 1T | 60 sec | 0.151 | 38 | X | | | | | X |
| 6-13 | 75% | 25% | 1% PP 3 mm | 65 | 2T | 30 sec | 0.147 | 41 | X | | | | | X |
| 6-14 | 75% | 25% | 1% PP 3 mm | 60 | 2T | 30 sec | 0.155 | 39 | X | | | | | X |
| 6-15 | 75% | 25% | 1% PP 3 mm | 55 | 2T | 60 sec | 0.157 | 41 | X | | | | | X |
| 6-16 | 100% | 0% | 4% PP 3 mm | 75 | 2T | 60 sec | 0.316 | 28 | X | | | | | X |
| 6-17 | 100% | 0% | 4% CF 3 mm | 75 | 2T | 60 sec | 0.219 | 55 | X | | | | | X |

*CF = Cellulose Fibers; PP 3 mm = Polypropylene fibers of 3 mm length

TABLE 7

Dispersion 4 (Flat-Side Molded Foam) by Drying Method 2

| Sample ID | Mold Type | Fibers (%) | Density (g/cm³) | Permeability (Darcies) | Visual Appearance | | | Softness | | |
|---|---|---|---|---|---|---|---|---|---|---|
| | | | | | Smooth | Few Cracks | Large Cracks | Soft | Medium | Firm |
| 7-1* | TEFLON | 0 | 0.061 | 110 | | X | | | X | |
| 7-2* | TEFLON | 1 | 0.077 | 140 | X | | | | | X |
| 7-3* | ALUMINUM | 0 | 0.082 | 47 | | X | | | X | |
| 7-4* | ALUMINUM | 1 | 0.071 | 56 | X | | | | X | |

*Foams are so friable that peeling the foams off the microcavitied-side mold results in some damage to the foams.

TABLE 8

Different Dispersion Mixture Percentage and Mold Type; Non-Compressed, Flat-Surfaced Foam

| Sample ID | % Dispersion | | Fibers (%) | Mold Type | Density (g/cm³) | Bending Modulus (N/m²) | Visual Appearance | | | Softness | | |
|---|---|---|---|---|---|---|---|---|---|---|---|---|
| | Dispersion 1 | Dispersion 2 | | | | | Smooth | Few Cracks | Large Cracks | Soft | Medium | Firm |
| 8-1 | 0 | 100 | 1 | TEFLON | 0.066 | 27 | X | | | X | | |
| 8-2 | 25 | 75 | 1 | TEFLON | 0.078 | 42.5 | X | | | X | | |
| 8-3 | 50 | 50 | 1 | TEFLON | 0.095 | 42.5 | X | | | X | | |
| 8-4 | 50 | 50 | 0.5 | TEFLON | 0.082 | 20.5 | X | | | X | | |
| 8-5 | 50 | 50 | 0.25 | TEFLON | 0.077 | 23 | X | | | X | | |
| 8-6 | 65 | 35 | 1 | TEFLON | 0.084 | 38 | X | | | | X | |
| 8-7 | 70 | 30 | 1 | TEFLON | 0.084 | 47 | X | | | | X | |
| 8-8 | 100 | 0 | 1 | TEFLON | 0.066 | 45 | | | X | | | X |
| 8-9 | 0 | 100 | 1 | Aluminum | 0.061 | 17.5 | X | | | X | | |
| 8-10 | 25 | 75 | 1 | Aluminum | 0.077 | 45 | X | | | X | | |
| 8-11 | 50 | 50 | 1 | Aluminum | 0.081 | 43 | X | | | X | | |
| 8-12 | 50 | 50 | 0.5 | Aluminum | 0.071 | 26 | X | | | X | | |
| 8-13 | 50 | 50 | 0.25 | Aluminum | 0.080 | 27 | X | | | X | | |
| 8-14 | 65 | 35 | 1 | Aluminum | 0.072 | 29.5 | X | | | | X | |
| 8-15 | 70 | 30 | 1 | Aluminum | 0.078 | 36.5 | X | | | | X | |
| 8-16 | 100 | 0 | 1 | Aluminum | 0.108 | 102.5 | | X | | | | X |

TABLE 9

Different Dispersion Mixture Percentage and Mold Type; for Non-Compressed, Microcavitied-Surfaced Foam

| Sample ID | % Dispersion Dispersion 1 | % Dispersion Dispersion 2 | Fibers (%) | Mold Type | Density (g/cm³) | Bending Modulus (N/m²) | Visual Appearance Smooth | Visual Appearance Few Cracks | Visual Appearance Large Cracks | Softness Soft | Softness Medium | Softness Firm |
|---|---|---|---|---|---|---|---|---|---|---|---|---|
| 9-1 | 25 | 75 | 1 | TEFLON | 0.066 | 20.5 | X | | | X | | |
| 9-2 | 50 | 50 | 1 | TEFLON | 0.064 | 12 | X | | | X | | |
| 9-3 | 50 | 50 | 0.5 | TEFLON | 0.056 | 2 | X | | | X | | |
| 9-4 | 50 | 50 | 0.25 | TEFLON | 0.055 | 3 | X | | | X | | |
| 9-5 | 65 | 35 | 1 | TEFLON | 0.058 | 12.5 | X | | | | X | |
| 9-6 | 70 | 30 | 1 | TEFLON | 0.064 | 9.5 | | X | | | X | |
| 9-7 | 100 | 0 | 0 | TEFLON | 0.051 | 13.5 | | | X | | X | |
| 9-8 | 25 | 75 | 1 | Aluminum | 0.055 | 21 | X | | | X | | |
| 9-9 | 50 | 50 | 1 | Aluminum | 0.060 | 17 | X | | | X | | |
| 9-10 | 50 | 50 | 0.5 | Aluminum | 0.052 | 10.5 | X | | | X | | |
| 9-11 | 50 | 50 | 0.25 | Aluminum | 0.053 | 8 | X | | | X | | |
| 9-12 | 65 | 35 | 1 | Aluminum | 0.054 | 12 | X | | | | X | |
| 9-13 | 70 | 30 | 1 | Aluminum | 0.059 | 16 | | X | | | X | |
| 9-14 | 100 | 0 | 1 | Aluminum | 0.087 | 39 | | X | | | | X |

Unless otherwise stated, in the following experiments the samples of foam were prepared in the manner described for Foam Preparation Method 2 and Drying Method 2 using either a Teflon or Aluminum mold and 1 wt. % PP 3 mm fiber based on total dispersion weight. Throughout Examples from 7 to 10 below a Dispersion 3 consisting of 50 percent Dispersion 1 and 50 percent Dispersion 2 was used for the foam composite preparation. The resultant foams were in all cases very uniform and have excellent flexibility and softness. In all cases, the SAP amount (Polymer A or Polymer B) was kept at 12 grams per composite pad. The SAP composite pad was then compressed with a set of shims with a thickness of 4.32 mm for a compression time of 60 seconds. The temperature and pressure were 65° C. and 2 tons, respectively. The compressed SAP composite foam pad (hereafter 'composite pad') was tested, or the composite pad was then inserted into the diaper chassis (hereafter 'Diaper') and then the Diaper was tested by cradle test.

EXAMPLE 7

Diaper Performance Test

The composite pad was prepared using foams molded in a Teflon mold, and the diaper containing the composite pad was tested. The diaper control was Huggies™ Supreme Size 4 (22-37 lbs/10-17 kg). The cradle test results for the composite pad sample diaper and diaper control are given in Table 10.

TABLE 10

Performances of Diaper and Diaper Control

| | Diaper Control Intake (sec) | Diaper Control Back-Wetting (g) | Diaper Control Wicking (cm) | Diaper Intake (sec) | Diaper Back-Wetting (g) | Diaper Wicking (cm) |
|---|---|---|---|---|---|---|
| 1st Insult | 8.9 | 0.1 | 10.5 | 17.6 | 4.8 | 12 |
| 2nd Insult | 10.2 | 3.9 | 12 | 11.8 | 10.2 | 14 |
| 3rd Insult | 12.3 | 12.3 | 15.5 | 12.4 | 17.4 | 17 |

The Diaper of this invention shows a better wicking than that of the Diaper control. Intake and back-wetting seem to be lowered by the lack of intimate contact between the composite pad surface and the intake layer.

EXAMPLE 8

Diaper and Composite Pad Performance Test

The composite pads were prepared using foams from aluminum molds. The performance of a composite pad and the Diaper were tested using the cradle test, and the results are given in Table 11.

TABLE 11

Performances of Diaper and Composite Pad

| | Diaper Intake (sec) | Diaper Back-Wetting (g) | Diaper Wicking (cm) | Composite Pad Intake (sec) | Composite Pad Back-Wetting (g) | Composite Pad Wicking (cm) |
|---|---|---|---|---|---|---|
| 1st Insult | 17.5 | 3.7 | 12 | 49.8 | 0.9 | 11 |
| 2nd Insult | 17.8 | 6.8 | 14 | 120.8 | 5.6 | 14 |
| 3rd Insult | 12.4 | 16.1 | 16 | 178.2 | 9.9 | 18 |

The composite pad of this invention showed better back-wetting, compared with the Diaper containing the same composite pad. Wicking for both the composite pad and Diaper were similar. Tests for intake time for the composite pad alone showed much higher values than those from the Diaper. This finding indicated that the intake layer of the Diaper plays a role for quick intake. Very high intake time for the composite pad was partly due to the thinness of the pad that limits contact with the liquid to be absorbed.

EXAMPLE 9

Diaper and Composite Pad Performance Test and Effects of Nonwovens and Perforation The composite pads in Table 12 were prepared using aluminum molded foams and contain a PP foam sheet and a non-woven tissue and were perforated. On the top of the SAP filled microcavitied-sided foam was placed a non-woven tissue of the same dimensions as the foam and having a thickness of approximately 180 microns and a density of 17.20 g/m², and then a PP foam sheet was placed on it to form the composite pad. The samples of composite pad and the Diaper containing the composite pad were tested using the cradle test. The results are given in Table 12.

TABLE 12

Performances of Diaper and Composite Pad: Effects of Nonwovens and Perforation

| | Diaper w/ Perforated Composite pad with Non-Woven Sheet | | | Perforated Composite Pad with Non-Woven Sheet | | |
|---|---|---|---|---|---|---|
| | Intake (sec) | Back-Wetting (g) | Wicking (cm) | Intake (sec) | Back-Wetting (g) | Wicking (cm) |
| 1st Insult | 13.4 | 3.2 | 11 | 50.1 | 0.3 | 11 |
| 2nd Insult | 13.0 | 6.4 | 14 | 79.0 | 4.5 | 16 |
| 3rd Insult | 12.5 | 12.6 | 17 | 218.1 | 8.0 | 21 |

Intake times for the composite pad showed high values, that was, the intake was slow due to the above-described small contact area of the pad. The results in Table 12 indicate that use of a perforated composite pad having a non-woven tissue layer improves not only the pad performance but also the overall Diaper performance, when compared with the results in Table 11.

EXAMPLE 10

Dip-and-Drip Diaper Test

Diaper Performance

Both the composite pads containing 12 grams and 16 grams of SAP, respectively, were prepared using a bottom sheet (Teflon-molded, microcavitied-side foam from Drying Method 2) and a thinner top sheet (flat-side foam from Drying Method 3). An average of 16 grams of SAP was found in the Diaper. As an additional comparative control, a Diaper containing foam composite pad without SAP particles was also prepared. Diapers containing the composite pads were dip-and-drip tested and compared with the Diaper control. The dip-and-drip test results for total absorption capacity of the Diaper containing the SAP composite foam pad and the Diaper control are given in Table 13.

TABLE 13

Total Absorption Capacity of Diapers

| | Diaper Control | Diaper with 12 grams of Polymer A | Diaper with 16 grams of Polymer A | Diaper Comparative/No SAP/w. Compression |
|---|---|---|---|---|
| Initial Weight (g) | 47.2 | 46.1 | 51.9 | 35.4 |
| Drip weight (g) | 773.2 | 674.3 | 857.3 | 148.6 |
| Absorption Amount (g) | 726.0 | 628.2 | 805.4 | 184.0 |
| SAP Amount (g) | 16 | 12 | 16 | N/A |
| Absorbency per gram of SAP | 45.4 | 52.4 | 50.3 | N/A |

N/A = Not applicable

Irrespective of the SAP amounts, the Diapers comprising the SAP composite foam pads of this invention showed a better absorbency per gram of SAP than that of the Diaper control, when total absorbency was measured by dip-and-drip testing.

EXAMPLE 11

Composite Pads of SAP and Foam Made from Dispersion 5 Using Drying Method 1 and Microcavity Incorporated Via Thermal Embossment (Thermoforming) Process and Liquid Absorption Tests Thermal embossed composite pad samples with and without SAP (Polymer A) were prepared, using Dispersion 5 and with Drying Method 1. A circular foam samples of 50 cm² area (diameter of 8.0 cm) with and without SAP (Polymer A) were prepared and subjected to MTS liquid absorption testing. The circular foam composite sample was weighed and an initial thickness was taken to determine density and initial thickness was recorded. The liquid absorption tests on the control circular foam sample without Polymer A (Examples 14-1A and 1B) and circular samples with Polymer A (14-2A and 2B) were conducted following the procedures as described above. The results are summarized in Table 14.

TABLE 14

Results for MTS Liquid Absorption Test on Composite Pads with and without SAP made via Laboratory Thermal Embossment (Thermoforming) Process using Aluminum Mold

| Sample ID | Thick (cm) | Weight (g) | Density (g/cm³) | 0.1 KpA Load | | 3 KpA Load | | 5 KpA Load | |
|---|---|---|---|---|---|---|---|---|---|
| | | | | Thick (cm) | Liquid Retained (g) | Thick (cm) | Liquid Retained (g) | Thick (cm) | Liquid Retained (g) |
| 14-1A | 0.333 | 0.989 | 0.059 | 0.333 | 20.2 | 0.133 | 12.2 | 0.133 | 10.9 |
| 14-1B | 0.339 | 1.001 | 0.059 | 0.339 | 19.0 | 0.139 | 11.0 | 0.139 | 9.5 |
| 14-2A | 0.360 | 2.644 | 0.147 | 0.460 | 21.5 | 0.260 | 20.2 | 0.26 | 20.2 |
| 14-2B | 0.367 | 2.634 | 0.144 | 0.467 | 22.2 | 0.267 | 20.3 | 0.267 | 20.3 |

The circular composite pads with SAP (Polymer A) clearly showed better liquid absorption and retention, compared with the control pads without SAP. While the control pads showed much stronger reduction of absorption with increasing pressure, the composite pads with SAP showed little reduction and keep higher absorption values.

EXEMPLARY EMBODIMENTS

Exemplary embodiments of the invention include, but are not limited to, the following.

Embodiment 1

A resilient foam comprising at least one thermoplastic polymer and containing a multiplicity of microcavities on or near at least one surface of the foam, which microcavities cumulatively comprise not more than 29 percent of the total volume of the foam.

Embodiment 2

The foam of Embodiment 1, further characterized in that a major portion the multiplicity of microcavities are located on the surface of the foam.

Embodiment 3

The foam of Embodiment 1, further characterized in that the microcavities of said foam cumulatively comprise not more than 18 percent of the total volume of the foam.

Embodiment 4

The foam of Embodiment 1, 2 or 3 further characterized in that the microcavities of said foam cumulatively comprise not less than 5 percent of the total volume of the foam.

Embodiment 5

The foam of Embodiment 1, 2 or 3, further characterized in that the microcavities of said foam cumulatively comprise not less than 9 percent of the total volume of the foam.

Embodiment 6

The foam of Embodiment 1 further characterized in that the at least one thermoplastic polymer is selected from interpolymers of ethylene and/or propylene, with or without other monomers selected from $C_4$ to $C_{20}$ alpha-olefin comonomers.

Embodiment 7

The foam of Embodiment 6, wherein the interpolymer has a Mw/Mn from about 1.5 to about 3.

Embodiment 8

The foam of Embodiment 6, wherein the interpolymer comprises: a catalytic linear multi-block olefin interpolymer; wherein the catalytic linear multi-block olefin interpolymer comprises at least one hard segment and at least one soft segment.

Embodiment 9

The foam of Embodiment 8, wherein the catalytic linear multi-block olefin interpolymer comprises from 5 to 70 weight percent of the at least one hard segment.

Embodiment 9

The foam of Embodiment 8, wherein the multi-block olefin interpolymer comprises from 15 to 60 weight percent of the at least one hard segment.

Embodiment 10

The foam of Embodiment 8, wherein the multi-block olefin interpolymer comprises at least one of an ethylene/α-olefin block interpolymer, a propylene/α-olefin block interpolymer, or combinations thereof.

Embodiment 11

The foam of Embodiment 8, wherein the at least one hard segment comprises from 0 to 5 weight percent α-olefin.

Embodiment 12

The foam of Embodiment 8, wherein the at least one soft segment comprises from 5 to 60 weight percent α-olefin.

Embodiment 13

The foam of Embodiment 8, wherein the multi-block olefin interpolymer comprises at least one polymer fraction obtained by preparative TREF, wherein the fraction has a block index from 0.3 to 1.0.

Embodiment 14

The foam of Embodiment 8, wherein the multi-block olefin interpolymer has a density d, in g/cc, and at least one melting point $T_m$, in °C., corresponding to the following relationship: $T_m > -2002.9 + 4538.5(d) - 2422.2(d)^2$.

Embodiment 15

The foam of Embodiment 8, wherein the multi-block olefin interpolymer has a density d, in g/cc, and at least one melting point $T_m$, in °C., corresponding to the following relationship: $T_m \geq 858.91 - 1825.3(d) + 1112.8(d)^2$.

Embodiment 16

The foam of Embodiment 1 further characterized in that the at least one thermoplastic polymer is an interpolymer of ethylene and at least one of 1-octene, 1-hexene, 4-methyl-1-pentene, 1-butene, isobutene or propylene.

Embodiment 17

The foam of Embodiment 1 further characterized in that the at least one thermoplastic polymer is a copolymer of ethylene and 1-octene.

Embodiment 18

The foam of Embodiment 1 further characterized in that at least some of the multiplicity of microcavities are of a substantially cylindrical shape.

Embodiment 19

The foam of Embodiment 1 further characterized in that the foam additionally comprises, dispersed therein, a multiplicity of fibers.

Embodiment 20

The foam of Embodiment 19 further characterized in that at least a portion of said fibers is selected from cellulosic or polypropylene fibers.

Embodiment 21

The foam of Embodiment 19 further characterized in that the average length of the multiplicity of fibers is greater than about 0.1 mm and less than about 15 mm, that the average thickness of the multiplicity of fibers is greater than about 0.001 mm and less than about 0.05 mm.

Embodiment 22

The foam of Embodiment 21 further characterized in that a majority of the fibers exhibit an average dtex that is greater than 0.5 and less than 50, preferably greater than 1.4 and less than 2.3.

Embodiment 23

The foam of Embodiment 1 further characterized in that the majority of the microcavities are of generally uniform size.

Embodiment 24

The foam of Embodiment 1 further characterized in that the microcavities are arranged in a substantially uniform pattern on or near the at least one surface of the foam.

Embodiment 25

A composite structure comprising the foam of Embodiment 1 further characterized in that a multiplicity of particles is substantially constrained within the multiplicity of microcavities in said foam.

Embodiment 26

The structure of Embodiment 25 further characterized in that the multiplicity of particles comprises at least 0.1 percent of the combined weight of said foam and said particles.

Embodiment 27

The structure of Embodiment 25 further characterized in that the multiplicity of particles comprises less than 80 percent of the combined weight of said foam and said particles.

Embodiment 28

The structure of Embodiment 26 or 27 further characterized in that the multiplicity of particles comprises fluid absorbent particles.

Embodiment 29

The structure of Embodiment 25 further characterized in that the multiplicity of particles comprises particles of a water-absorbent polymer.

Embodiment 30

The structure of Embodiment 25 further characterized in that the multiplicity of particles comprise particles of a of water-absorbent polymer, which are selected from particles of an acrylic interpolymer comprising at least one ethylenically unsaturated monomer selected from acrylic acid, methacrylic acid and salts of said acids.

Embodiment 31

The structure of Embodiment 30 further characterized in that the particles of water-absorbent polymer further comprise one or more comonomers or graft substrates known in the art for use in making superabsorbent polymers or graftcopolymers, such comonomers being selected from an acrylamide, an acrylonitrile, a vinyl pyrrolidone, a vinyl sulphonic acid or a salt thereof, and the graft substrate for graftcopolymers being selected from a cellulose, a modified cellulose or a starch hydrolyzate, where the comonomers comprise up to 25 percent of the dry weight of the water-absorbent polymer.

Embodiment 32

The structure of Embodiment 30 characterized by the particles of water-absorbent polymer having from about 30, preferably from about 50 percent up to about 100 percent, preferably up to about 80 percent of its acid moieties neutralized to their respective salt.

Embodiment 33

The structure of Embodiment 32 characterized by the acid salt moieties of the particles of water-absorbent polymer being in the form of a Group I metal ion salt, preferably a sodium or potassium salt.

Embodiment 34

The structure of Embodiment 32 characterized by the particles of water-absorbent polymer having a centrifuge retention capacity as measured in 0.9 wt. % NaCl solution, based on dry weight of said particles, that is less than about 70 g/g, preferably less than about 60 g/g, and more preferably less than about 50 g/g.

Embodiment 35

The structure of Embodiment 32 characterized by the particles of water-absorbent polymer having a centrifuge retention capacity as measured in 0.9 wt. % NaCl solution, based on dry weight of said particles, that is greater than about 10 g/g, preferably greater than about 20 g/g, and more preferably greater than about 30 g/g.

Embodiment 36

The structure of Embodiment 29 further characterized by the particles of water-absorbent polymer being present in an amount, dry weight basis, of at least about 0.1, preferably at least about 10, more preferably at least about 20, even more preferably at least about 30, and most preferably at least about 40 weight percent and not more than about 80, preferably not more than about 70, more preferably not more than about 60, even more preferably not more than about 50, and most preferably not more than about 45 weight percent, based on dry weight of the polymer and the total weight of the structure.

Embodiment 37

The structure of Embodiment 29 further characterized by the particles of water-absorbent polymer, prior to their incorporation into the microcavities of the foam, having been treated in a process to control their centrifuge retention capacity, as measured in 0.9 wt. % NaCl solution, based on dry weight of said particles, to between about 20 g/g and about 60 g/g and that process of treatment is selected from one or more of the group consisting of heat-treating, surface crosslinking and ionic crosslinking.

Embodiment 38

The structure of Embodiment 25, 26 or 27 further characterized in that the multiplicity of particles comprises particles of a water-absorbent polymer, such particles of water-absorbent polymer having an absorption under load (AUL) as measured in 0.9 wt. % NaCl solution and under pressure of 0.3 psi that, based on dry weight of said particles, is less than about 50 g/g, preferably less than about 40 g/g, and more preferably less than about 30 g/g, and that is greater than about 10 g/g, preferably greater than about 15 g/g, and more preferably greater than about 20 g/g.

Embodiment 39

The structure of Embodiment 38 further characterized by the particles of water-absorbent polymer, prior to their incorporation into the microcavities of the foam, having been treated in order to control their AUL to between about 15 and about 40 g/g, and that such treatment is selected from one or more of the group consisting of heat-treating, surface crosslinking and ionic crosslinking.

Embodiment 40

The structure of Embodiment 25, 26 or 27 further characterized by the particles of water-absorbent polymer having a size, dry basis, as measured with sieve analysis that is less than about 1000 microns, preferably less than about 800 microns, and more preferably less than about 600 microns, and that is greater than about 35 microns, preferably greater than about 100 microns, and more preferably greater than about 300 microns.

Embodiment 41

The structure of Embodiment 37 further characterized by the particles of water-absorbent polymer having been surface modified with fine particles of inorganic or organic nature selected from fumed silica, Magadiite and modified Magadiite, silicates, calcium carbonate, titanium dioxide, clays, cyclodextrin, activated carbon, zeolites, chlorophyllin, water-soluble polymers, biocides, and odor control agents that have been added either directly to the raw materials used to prepare the foam or added to and contained in the microcavities of the foam.

Embodiment 42

The structure of Embodiment 41 further characterized by the fine particles of inorganic or organic nature having been selected with the morphology of platelets, tubes of different characteristic length (e.g., nano-carbon tubes), cylinders, polycylinders, spheres, balls (e.g., fullerene types), polyhedrals, discs, needles, polyneedles, cubes, irregular shapes and ellipsoids.

Embodiment 43

The structure of Embodiment 25 further characterized by having a multiplicity of fibers made from cellulosic base stock (e.g., cotton linters/staple fibers) or polymeric synthetic fibers such as polypropylene, such fibers having been incorporated in the foam and providing added strength and flexural modulus to the foam, or reducing or eliminating cracking in the foam, when compared to these properties the same foam prepared without the incorporation of such fibers.

Embodiment 44

The structure of Embodiment 29 further characterized by the foam component, either before or after incorporation in the structure, having been subjected to a heat-compression treatment where the heat-compression is conducted at a temperature of at least 50° C., preferably at a temperature of at least 55° C. and more preferably at a temperature of at least 65° C., and below 90° C., preferably below 80° C. and more preferably below 70° C.

Embodiment 45

The structure of Embodiment 44 further characterized in that the compressed foam and particles of water-absorbent polymer form a composite and wherein the composite has been perforated to form holes on at least a portion of the composite's surfaces.

Embodiment 46

The structure of Embodiment 25 further characterized in that the multiplicity of particles comprises, at least in part, an odor control agent.

Embodiment 47

A hygiene article comprising, as a component, the composite structure of Embodiment 25.

Embodiment 48

The hygiene article of Embodiment 47 further characterized in that the multiplicity of particles comprises fluid absorbent particles and by its selection from an infant diaper, an adult incontinency article and a feminine menses-absorbing article, wherein an insult absorbing element of the hygiene article comprises at least said composite structure.

Embodiment 49

The article of Embodiment 48 further characterized in that the foam of the composite structure comprises at least one copolymer of ethylene and 1-octene; the microcavities cumulatively comprise at least 5% of the total volume of the foam; and the multiplicity of particles primarily comprises particles prepared from an interpolymer comprising acrylic acid and at least its sodium or potassium salt.

Embodiment 50

The hygiene article of Embodiment 47 further characterized in that the resilient foam of the composite structure comprises at least one copolymer of ethylene and 1-octene; and the microcavities cumulatively comprise at least 5% of the total volume of the foam.

Embodiment 51

The hygiene article of Embodiment 47 further characterized in that said article exhibits an absorbency, dry basis, per gram of the particles of the water-absorbent polymer in the composite structure exceeds, when measured by dip-and-drip testing, 46 grams, preferably 50 grams and more preferably 52 grams, of 0.9% saline solution.

Embodiment 52

An aqueous liquid adsorptive article, comprising as at least one element the composite structure of Embodiment 25, and characterized by selection from a pet urine-absorption pad, a pet urine-absorption mat and a household cleaning pad.

Embodiment 53

The article of Embodiment 52 further characterized in that the multiplicity of particles comprises particles of a water-absorbent polymer.

Embodiment 54

A hygiene article characterized as an infant diaper, such article comprising an insult absorbing element that comprises at least one composite structure comprising a resilient foam, which foam comprises at least one interpolymer of, by weight, 80 percent ethylene and 20 percent 1-octene and contains a multiplicity of microcavities on or near at least one surface of the foam, which microcavities cumulatively comprise at least 7 percent and not more than 14 percent of the total volume of the foam, characterized in that a multiplicity of particles is substantially contained within said multiplicity of microcavities, and further characterized in that the multiplicity of particles comprises on a dry weight basis at least 35 percent and not greater than 55 percent of the combined weight of said foam and said particles, and further characterized in that the multiplicity of particles comprises particles of a water-absorbent polymer that is selected from interpolymers comprising acrylic acid and at least one of its sodium or potassium salts and, based on the dry weight of such water-absorbent particles, has a centrifuge retention capacity as measured in 0.9 wt. % NaCl solution that is less than about 50 g/g, but that is greater than about 25 g/g and also has an absorption under load, as measured in 0.9 wt. % NaCl solution and under pressure of 0.3 psi, that is less than about 40 g/g but that is greater than about 15 g/g, and that the hygiene article is further characterized by said article having an absorbency per gram (dry weight) of particles of the water-absorbent polymer in the microcavities of the foam composite structure that exceeds, when measured by dip-and-drip testing, 46 grams of 0.9% saline solution.

Embodiment 55

The foam of Embodiment 1, wherein said foam having a compression set at 85° C., 20 minutes, at a pressure of 0.5 psig of less than 70 percent.

Embodiment 56

The foam of Embodiment 1, having a compression set at 85° C., 20 minutes, at a pressure of 0.1 psig of less than 45 percent.

Embodiment 57

The foam of Embodiment 1, comprising cells having a size ranging from about 5 micrometers diameter to about 1000 micrometers diameter.

Embodiment 58

The foam of Embodiment 57, wherein the cells comprise open cells.

Embodiment 59

The foam of Embodiment 58, wherein the cells comprise open cells.

Embodiment 60

A method of forming a froth foam, comprising the following steps: (1) providing a dispersion; (2) contacting the dispersion with air or other inert gas to form a whipped dispersion; (3) depositing the whipped dispersion onto a substrate; and (4) at least partially drying the whipped dispersion to form a frothed foam; wherein the whipped dispersion is formed at a temperature less than the melting point of the dispersed polymers of said dispersion, more preferably at about 25 C+/−10 C.

Embodiment 61

The method of forming the froth foam of Embodiment 60, wherein the whipped dispersion has a volume of at least 20% greater than the dispersion prior to contacting with air or other inert gas.

Embodiment 61

The method of forming the froth foam of Embodiment 60, wherein the whipped dispersion has a density at least 5% lower than the dispersion prior to contacting with air or other inert gas.

We claim:
1. An open cell foam derived from a frothed aqueous dispersion, wherein said frothed aqueous dispersion comprises:
   an aqueous thermoplastic polymer dispersion and one or more entrained gases or air; and
   wherein, prior to frothing, the aqueous thermoplastic polymer dispersion comprises:
   at least one thermoplastic polymer, wherein said thermoplastic polymer is selected from interpolymers of ethylene and/or propylene, with or without other monomers selected from $C_4$ to $C_{20}$ alpha-olefin comonomers;

a dispersant; and
water; and
wherein the at least one thermoplastic polymer is dispersed in the water as polymer particles having a particle size from above 5 to 25 microns;
wherein said open cell foam further comprises a plurality of microcavities arranged in a substantially uniform pattern on or near at least one of its surfaces;
wherein the open cell foam is free of fibers.

2. The open cell foam of claim 1, wherein said plurality of microcavities comprise at least 7 percent of the total volume of said open cell foam.

3. The open cell foam of claim 2, wherein said plurality of microcavities comprise less than 29 percent of the total volume of said open cell foam.

4. The open cell foam of claim 1, wherein said open cell foam further comprises a plurality of particles, and said plurality of particles are substantially contained within said plurality of microcavities.

5. The open cell foam of claim 4, wherein said open cell foam comprises about at least 35 percent by the total weight of said plurality of particles, based on the combined weight of said open cell foam and said plurality of particles.

6. The open cell foam of claim 1, wherein said interpolymer has a Mw/Mn from about 1.5 to about 3.

7. The open cell foam of claim 1, wherein said interpolymer comprises a catalytic linear multi-block olefin interpolymer including at least one hard segment and at least one soft segment.

8. The open cell foam of claim 1, wherein said thermoplastic polymer is an interpolymer of ethylene and at least one of 1-octene, 1-hexene, 4-methyl-1-pentene, 1-butene, isobutene or propylene.

9. An article comprising the open cell foam of claim 1.

10. The article of claim 9, wherein said open cell foam further comprises a plurality of particles, and said plurality of particles are substantially contained within said plurality of microcavities, and wherein said plurality of particles comprise at least 0.1 percent of the combined weight of said foam and said particles.

11. The article of claim 10, wherein said plurality of particles comprise less than 80 percent of the combined weight of said foam and said particles.

12. The article of claim 10, wherein said plurality of particles are fluid absorbent particles.

13. The article of claim 12, wherein said fluid absorbent particles are surface modified with fine particles of inorganic or organic nature selected from the group consisting of fumed silica, Magadiite, modified Magadiite, silicates, calcium carbonate, titanium dioxide, clays, cyclodextrin, activated carbon, zeolites, chlorophyllin, water-soluble polymers, biocides, and odor control agents.

14. A hygiene article comprising:
the article according to claim 9, wherein said open cell foam further comprises a plurality of particles, and said plurality of particles are substantially contained within said plurality of microcavities; wherein said plurality of particles comprise at least 0.1 percent of the combined weight of said foam and said particles; and wherein said plurality of particles are fluid absorbent particles.

15. An infant diaper comprising:
the article according to claim 9, wherein said open cell foam further comprises a plurality of particles, and said plurality of particles are substantially contained within said plurality of microcavities; wherein said plurality of particles comprise at least 0.1 percent of the combined weight of said foam and said particles; and wherein said plurality of particles are fluid absorbent particles.

16. An adult incontinency article comprising:
the article according to claim 9, wherein said open cell foam further comprises a plurality of particles, and said plurality of particles are substantially contained within said plurality of microcavities; wherein said plurality of particles comprise at least 0.1 percent of the combined weight of said foam and said particles; and wherein said plurality of particles are fluid absorbent particles.

17. A feminine menses-absorbing article comprising:
the article according to claim 9, wherein said open cell foam further comprises a plurality of particles, and said plurality of particles are substantially contained within said plurality of microcavities; wherein said plurality of particles comprise at least 0.1 percent of the combined weight of said foam and said particles; and wherein said plurality of particles are fluid absorbent particles.

* * * * *